(12) United States Patent
Noordam et al.

(10) Patent No.: US 9,982,280 B2
(45) Date of Patent: *May 29, 2018

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventors: Bertus Noordam, Echt (NL); Michael Petrus Jozef Berkhout, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/440,662

(22) PCT Filed: Nov. 7, 2013

(86) PCT No.: PCT/EP2013/073255
§ 371 (c)(1),
(2) Date: May 5, 2015

(87) PCT Pub. No.: WO2014/072395
PCT Pub. Date: May 15, 2014

(65) Prior Publication Data
US 2015/0307903 A1    Oct. 29, 2015

(30) Foreign Application Priority Data

| Nov. 9, 2012 | (EP) | 12191957 |
|---|---|---|
| Jul. 2, 2013 | (EP) | 13174656 |
| Jul. 11, 2013 | (EP) | 13176083 |
| Jul. 15, 2013 | (EP) | 13176500 |
| Sep. 17, 2013 | (EP) | 13184701 |
| Sep. 17, 2013 | (EP) | 13184702 |

(51) Int. Cl.

| C12P 7/10 | (2006.01) |
|---|---|
| C12P 7/16 | (2006.01) |
| C12P 7/18 | (2006.01) |
| C12P 7/20 | (2006.01) |
| C12P 7/40 | (2006.01) |
| C12P 7/42 | (2006.01) |
| C12P 7/46 | (2006.01) |
| C12P 7/48 | (2006.01) |
| C12P 7/54 | (2006.01) |
| C12P 7/56 | (2006.01) |
| C12P 17/10 | (2006.01) |
| C12P 19/02 | (2006.01) |
| C12P 19/14 | (2006.01) |

(Continued)

(52) U.S. Cl.
CPC ............. *C12P 7/10* (2013.01); *C12P 5/026* (2013.01); *C12P 7/16* (2013.01); *C12P 7/18* (2013.01); *C12P 7/20* (2013.01); *C12P 7/40* (2013.01); *C12P 7/42* (2013.01); *C12P 7/46* (2013.01); *C12P 7/48* (2013.01); *C12P 7/54* (2013.01); *C12P 7/56* (2013.01); *C12P 17/10* (2013.01); *C12P 19/02* (2013.01); *C12P 19/14* (2013.01); *C12P 35/00* (2013.01); *C12P 2203/00* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| 2009/0035826 A1* | 2/2009 | Tolan | B01D 3/001 435/99 |
|---|---|---|---|
| 2010/0304437 A1* | 12/2010 | Garner | C12N 9/2437 435/72 |

(Continued)

FOREIGN PATENT DOCUMENTS

| CN | 102325889 A | 1/2012 |
|---|---|---|
| CN | 102459582 A | 5/2012 |
| EP | 0058426 A1 | 8/1982 |

(Continued)

OTHER PUBLICATIONS

Phillips et al., American Chemical Society Chemical Biology, vol. 6, No. 12, pp. 1399-1406 (electronically published Oct. 17, 2011).*

(Continued)

*Primary Examiner* — Soren Harward
*Assistant Examiner* — Paul D. Pyla
(74) *Attorney, Agent, or Firm* — McBee Moore Woodward & Vanik IP, LLC; Susan McBee; Chester Moore

(57) ABSTRACT

The invention relates to a process for the preparation of a fermentation product from ligno-cellulosic material, comprising the following steps:

a) optionally pre-treatment of the ligno-cellulosic material;

b) optionally washing of the optionally pre-treated ligno-cellulosic material;

c) enzymatic hydrolysis of the optionally washed and/or optionally pre-treated ligno-cellulosic material using an enzyme composition comprising at least two cellulase and whereby the enzyme composition at least comprises GH61;

d) whereby less than 7.5 mg enzyme composition/g glucan (on dry matter and enzyme as protein) or less than 3.0 mg enzyme composition/g feedstock (on dry matter and enzyme as protein) is used; and e) fermentation of the hydrolysed ligno-cellulosic material to produce a fermentation product; and f) optionally recovery of a fermentation product;

wherein before and/or during the enzymatic hydrolysis oxygen is added to the ligno-cellulosic material.

28 Claims, 6 Drawing Sheets

(51) Int. Cl.
C12P 35/00 (2006.01)
C12P 5/02 (2006.01)

(56) References Cited

U.S. PATENT DOCUMENTS

2012/0114797 A1 5/2012 Perkins et al.
2015/0315622 A1 11/2015 Frickmann et al.

FOREIGN PATENT DOCUMENTS

| WO | 01/60752 A1 | 8/2001 | |
|---|---|---|---|
| WO | 2007091231 A1 | 8/2007 | |
| WO | 2008008793 A2 | 1/2008 | |
| WO | 2009/055793 A1 | 4/2009 | |
| WO | 2009046538 A1 | 4/2009 | |
| WO | 2010/138754 A1 | 2/2010 | |
| WO | 2010080407 A2 | 7/2010 | |
| WO | 2011/000949 A1 | 1/2011 | |
| WO | WO 2011000949 A1 * | 1/2011 | ........... C12N 9/2437 |
| WO | 2012/061517 A1 | 5/2012 | |
| WO | 2012/088429 A2 | 6/2012 | |
| WO | 2014/072392 A1 | 5/2014 | |
| WO | 2014/072393 A1 | 5/2014 | |
| WO | 2015/075277 A1 | 5/2015 | |

OTHER PUBLICATIONS

Podkaminer et al., Biotechnology for Biofuels, vol. 5, pp. 43-51 (published Jun. 15, 2012)(of record).*
Phillips et al., American Chemical Society Chemical Biology, vol. 6, No. 12, pp. 1399-1406 (electronically published Oct. 17, 2011)(of record).*
Sweeney, Matt D. et al., "Biomass Converting Enzymes as Industrial Biocatalysts for Fuels and Chemicals: Recent Developments", Catalysts, Apr. 12, 2012, pp. 244-263.
Quinlan, R, Jason et al., "Insights Into the Oxidative Degradation of Cellulose by a Copper Metalloenzyme That Exploits Biomass Components", PNAS, Sep. 13, 2011, pp. 15079-15084, vol. 108, No. 37.
Horn et al,, "Novel Enzymes for the Degradation of Cellulose", Biotechnology for Biofuels, Jul. 2, 2012, pp. 45(1)-56(12), vol. 5, XP021122735.
Cannella et al., "Production and effect of aldonic acids during enzymatic hydrolysis of lignocellulose at high dry matter content." Biotechnology for Biofuels 2012, 5:26.
Canella et al., "Do New Cellulolytic Enzyme Preparations Affect the Industrial Strategies for High Solids Lignocellulosic Ethanol Production?" XP-002721360. Biotechnology and Bioengineering 2014, 111:1.
Kumar et al., "Recent Advances in Production of Bioethanol from Lignocellulosic Biomass." Chem. Eng. Technol. (2009) 32(4) 517-526.
Badger, "Ethanol From Cellulose: A General Review." Reprinted from: Trends in new crops and new uses. 2002.
International Search Report from corresponding PCT/EP2013/073255, dated Jan. 23, 2014.
Podkaminer et al., Ethanol and anaerobic conditions reversibly inhibit commercial cellulase activity in thermophilic simultaneous saccharification and fermentation (tSSF), Biotechnology for Biofuels, 2012, pp. 1-9, XP021108101.
Bey, "Cello-Oligosaccharide Oxidation Reveals Differences between Two Lytic Polysaccharide Monooxygenases (Family GH61) from Podospora anserina", Applied and Environmental Microbiology, p. 488-696, Jan. 2013, vol. 79, No. 2, XP008160285.
Kostylev et al., "Synergistic interactions in cellulose hydrolysis", Future Science Ltd., ISSN 1759-7629, pp. 61-70, XP-002693861.
Viikari et al., "Lignocellulosic ethanol: From science to industry", Elsevier, SciVerse ScienceDirect, Biomass and Bioenergy 46 (2012) pp. 13-24, XP-002718612.
Levasseur et al, Expansion of hte enzymatic repertoire of the CAZy database to integrate auxiliary redox enzymes, Biotechnology for Biofuels, 2013, pp. 1-14, XP0021147399.
Badger, "Ethanol from Cellulose: A General Review", Trends in new crops and new uses, 2002, ASHS Press, Alexandria, VA, 5 pages.
Kumar et al., "Recent Advances in Production of Bioethanol from Lignoellulosic Biomass", Chem. Eng. Technol. 2009, 32, No. 4, pp. 517-526.
Hu et al., "The synergistic action of accessory enzymes enhances the hydrolytic potential of a "cellulase mixture" but is highly sustrate specific", Biotechnology for Biofuels 2013, 6:112, XP21158122A; pp. 1-12.
International Search Report of International Patent Application No. PCT/EP2013/073250 dated Jan. 8, 2014.
Deng et al., "Influence of culture aeration on the cellulase activity of Thermobifida fusca", Appl Microbial Biotechnol (2010), Biotechnological Products and Process Engineering, pp. 965-974, XP19773511.
International Search Report of International Patent Application No. PCT/EP2015/051839 dated Apr. 28, 2016.
International Search Report of International Patent Application No. PCT/EP2013/073253 dated Mar. 21, 2014.
International Search Report of International Patent Application No. PCT/EP2015/059317 dated Jul. 20, 2015.
Ioelovich et al., "Study of Enzymatic Hydrolysis of Pretreated Biomass at Increased Solids Loading." Bio Resources (2012), 7(4), 4672-4682.

* cited by examiner

PROCESS FOR ENZYMATIC HYDROLYSIS OF LIGNOCELLULOSIC MATERIAL AND FERMENTATION OF SUGARS

CROSS REFERENCE TO RELATED APPLICATION

This application is a § 371 National Stage Application of PCT/EP2013/073255, filed 7 Nov. 2013, which claims priority to EP 12191957.5, filed 9 Nov. 2012, EP 13174656.2, filed 2 Jul. 2013, EP 13176083.7, filed 11 Jul. 2013, EP 13176500.0, filed 15 Jul. 2013, EP 13184702.2, filed 17 Sep. 2013 and EP 13184701.4, filed 17 Sep. 2013.

BACKGROUND

Field of the Invention

The invention relates to a process for the enzymatic hydrolysis of lignocellulosic material and fermentation of sugars.

Description of Related Art

Ligno-cellulosic plant material, herein also called feedstock, is a renewable source of energy in the form of sugars that can be converted into valuable products e.g. sugars or bio-fuel, such as bio-ethanol. During this process, (ligno or hemi)-cellulose present in the feedstock, such as wheat straw, corn stover, rice hulls, etc., is converted into reducing sugars by (hemi)-cellulolytic enzymes, which then are optionally converted into valuable products such as ethanol by microorganisms like yeast, bacteria and fungi.

Since the (hemi)-cellulose is crystalline and entrapped in a network of lignin the conversion into reducing sugars is in general slow and incomplete. Typically, enzymatic hydrolysis of untreated feedstock yields sugars <20% of theoretical quantity. By applying a chemical and thermo-physical pre-treatment, the (hemi)-cellulose is more accessible for the (hemi)-cellulolytic enzymes, and thus conversions go faster and at higher yields.

A typical ethanol yield from glucose, derived from pre-treated corn stover, is 40 gallons of ethanol per 1000 kg of dry corn stover (Badger, P, Ethanol from cellulose: a general review, Trends in new crops and new uses, 2002, J. Janick and A. Whipkey (eds.) ASHS Press, Alexandria, Va.) or 0.3 g ethanol per g feedstock. The maximum yield of ethanol on cellulose base is approximately 90%.

Cellulolytic enzymes-most of them are produced by species like *Trichoderma, Humicola* and *Aspergillus*—are commercially used to convert pre-treated feedstock into a mash containing insoluble (hemi)cellulose, reducing sugars made thereof, and lignin. Thermostable cellulolytic enzymes derived from *Rasamsonia*, have been used for degrading ligno-cellulosic feedstock and these enzymes are known for their thermostability, see WO2007091231. The produced mash is used in a fermentation during which the reducing sugars are converted into yeast biomass (cells), carbon dioxide and ethanol. The ethanol produced in this way is called bio-ethanol.

The common production of sugars from pre-treated ligno-celullosic feedstock, the hydrolysis also called liquefaction, pre-saccharification or saccharification, typically takes place during a process lasting 6 to 168 hours (Kumar, S. , Chem. Eng. Technol. 32 (2009) 517-526) under elevated temperatures of 45 to 50° C. and non-sterile conditions. During this hydrolysis, the cellulose present is partly (typically 30 to 95%, dependable on enzyme activity and hydrolysis conditions) converted into reducing sugars. In case of inhibition of enzymes by compounds present in the pre-treated feedstock and by released sugars; and to minimize thermal inactivation, this period of elevated temperature is minimized as much as possible.

The fermentation following the hydrolysis takes place in a separate preferably anaerobic process step, either in the same or in a different vessel, in which temperature is adjusted to 30 to 33° C. (mesophilic process) to accommodate growth and ethanol production by microbial biomass, commonly yeasts. During this fermentation process, the remaining (hemi) cellulosic material is converted into reducing sugars by the enzymes already present from the hydrolysis step, while microbial biomass and ethanol are produced. The fermentation is finished once (hemi) cellulosic material is converted into fermentable sugars and all fermentable sugars are converted into ethanol, carbon dioxide and microbial cells. This may take up to 6 days. In general the overall process time of hydrolysis and fermentation may amount up to 13 days.

The so obtained fermented mash consists of non-fermentable sugars, non-hydrolysable (hemi) cellulosic material, lignin, microbial cells (most common yeast cells), water, ethanol, dissolved carbon dioxide. During the successive steps, ethanol is distilled from the mash and further purified. The remaining solid suspension is dried and used as, for instance, burning fuel, fertilizer or cattle feed.

WO2010080407 suggests treating cellulosic material with a cellulase composition under anaerobic conditions. Removal or exclusion of reactive oxygen species may improve the performance of cellulose-hydrolyzing enzyme systems. Hydrolysis of cellulosic material, e.g., lignocellulose, by an enzyme composition can be reduced by oxidative damage to components of the enzyme composition and/or oxidation of the cellulosic material by, for example, molecular oxygen.

WO2009046538 discloses a method for treating lignocellulosic feedstock plant materials to release fermentable sugars using an enzymatic hydrolysis process for treating the materials performed under vacuum and producing a sugar rich process stream comprising reduced amounts of volatile sugar/fermentation inhibiting compounds such as furfural and acetic acid. Apart from removing volatile inhibitory compounds, other compounds and/or molecules that are also removed include nitrogen, oxygen, argon and carbon dioxide.

With each batch of feedstock, enzymes are added to maximize the yield and rate of fermentable sugars released from the pre-treated ligno-cellulosic feedstock during the given process time. In general, costs for enzymes production, feedstock to ethanol yields and investments are major cost factors in the overall production costs (Kumar, S. Chem. Eng. Technol. 32 (2009) 517-526). Thus far, cost of enzyme usage reduction is achieved by applying enzyme products from a single or from multiple microbial sources (WO 2008/008793) with broader and/or higher (specific) hydrolytic activity which use aims at a lower enzyme need, faster conversion rates and/or a higher conversion yields, and thus at overall lower bio-ethanol production costs. This requires large investments in research and development of these enzyme products. In case of an enzyme product composed of enzymes from multiple microbial sources, large capital investments are needed for production of each single enzyme compound.

It is therefore desirable to improve the above process involving hydrolysis and fermentation.

SUMMARY

An object of the invention is therefore to provide a process in which the hydrolysis step is conducted at improved conditions. Another object of the invention is to provide a process involving hydrolysis having a reduced process time. Further object of the invention is to provide a process, wherein the dosage of enzyme may be reduced and at the same time output of useful hydrolysis product is maintained at the same level or even increased. Another object is to provide a process involving hydrolysis, wherein the process conditions of the hydrolysis are optimized. A still further object of the invention is to provide a process involving hydrolysis, wherein the output of useful hydrolysis product is increased using the same enzyme dosage. One or more of these objects are attained according to the invention.

The present invention provides a process for the preparation of a sugar product from ligno-cellulosic material, comprising the following steps:
- a) optionally pre-treatment of the ligno-cellulosic material;
- b) optionally washing of the optionally pre-treated ligno-cellulosic material;
- c) enzymatic hydrolysis of the optionally washed and/or optionally pre-treated ligno-cellulosic material using an enzyme composition comprising at least two cellulases and whereby the enzyme composition at least comprises GH61;
- d) whereby less than 7.5 mg enzyme composition/g glucan (on dry matter and enzyme as protein) or less than 3.0 mg enzyme composition/g feedstock (on dry matter and enzyme as protein) is used; and
- e) optionally recovery of a sugar product;

wherein after the pre-treatment and before and/or during the enzymatic hydrolysis oxygen is added to the ligno-cellulosic material.

Preferably during the enzymatic hydrolysis step c) oxygen is added to the ligno-cellulosic material.

According to an embodiment of the invention during part of the time of the enzymatic hydrolysis, oxygen is added to the ligno-cellulosic material and during part of the time of the enzymatic hydrolysis less oxygen is added to the ligno-cellulosic material compared to the other part of the time of the enzymatic hydrolysis, preferably no oxygen is added to the ligno-cellulosic material.

Furthermore the present invention provides a process for the preparation of a fermentation product from ligno-cellulosic material, comprising the following steps:
- a) optionally pre-treatment of the ligno-cellulosic material;
- b) optionally washing of the optionally pre-treated ligno-cellulosic material;
- c) enzymatic hydrolysis of the optionally washed and/or optionally pre-treated ligno-cellulosic material using an enzyme composition comprising at least two cellulases and whereby the enzyme composition at least comprises GH61;
- d) fermentation of the hydrolysed ligno-cellulosic material to produce a fermentation product;
- e) whereby less than 7.5 mg enzyme composition/g glucan (on dry matter and enzyme as protein) or less than 3.0 mg enzyme composition/g feedstock (on dry matter and enzyme as protein) is used; and
- f) optionally recovery of a fermentation product;

wherein after the pre-treatment and before and/or during the enzymatic hydrolysis oxygen is added to the ligno-cellulosic material.

Preferably during the enzymatic hydrolysis step c) oxygen is added to the ligno-cellulosic material.

According to an embodiment of the invention during part of the time of the enzymatic hydrolysis, oxygen is added to the ligno-cellulosic material and during part of the time of the enzymatic hydrolysis less oxygen is added to the ligno-cellulosic material compared to the other part of the time of the enzymatic hydrolysis, preferably no oxygen is added to the ligno-cellulosic material.

According to a preferred embodiment of the invention the part of the time wherein less or preferably no oxygen is added is 10 to 80%, preferably 20 to 80%, more preferably 30 to 80% and most preferably 40 to 80% of the total enzymatic hydrolysis time.

According to another preferred embodiment of the invention the part of the time wherein more oxygen is added is 2 to 80%, preferably 4 to 60%, more preferably 8 to 50% and most preferably 10 to 50% of the total enzymatic hydrolysis time, more preferably the part of the time wherein more oxygen is added is
- a) 12 to 50%, and preferably 20 to 40% when the oxygen is added in the second half of time of the enzymatic hydrolysis;
- b) 2 to 30%, preferably 4 to 25% and more preferably 5 to 20% of the total enzymatic hydrolysis time when the oxygen is added in the first half of time of the enzymatic hydrolysis; or
- c) or a combination of a and b.

Advantageously the oxygen concentration in the liquid phase of the hydrolysis during the part of the time wherein oxygen is added is at least 2 times, preferably at least 4 times, more preferably at least 10 times the oxygen concentration in the liquid phase during the part of the time wherein less or no oxygen is added.

According to a further preferred embodiment of the invention, in the part of the time when the oxygen is added, the oxygen concentration in the liquid phase, wherein the ligno-cellulosic material is present during the enzymatic hydrolysis, is at least $0.001$ mol/m$^3$, preferably at least $0.002$ mol/m$^3$ and most preferably at least $0.003$ mol/m$^3$ and even more preferably more than $0.01$ mol/m$^3$, for example more than $0.02$ mol/m$^3$ or $0.03$ mol/m$^3$. In reactors of less than 1 m$^3$ DO values of below $0.01$ mol/m$^3$ or $0.02$ mol/m$^3$ will be obtained by slow stirring. Vigorous mixing or stirring at such scale introduces part of the gas phase of the headspace into the reaction liquid. For example the mixing or stirring may create a whirlpool that draws oxygen into the liquid. In general flushing the headspace with air in combination with (vigorous) mixing or stirring will introduce sufficient oxygen into the cellulosic material in the hydrolysis reactor for reactors up to a size of 100 liter to 1 m$^3$. At larger scale, for example in a reactor of 50 m$^3$ or more, for example 100 m$^3$, so much energy is needed for vigorous stirring that from economic point of view this will not be applied in a commercially operating process. In general in large reactors, stirring or mixing without introducing air or oxygen will result in DO values of less than $0.01$ mol/m$^3$.

To still another preferred embodiment of the invention during the oxygen addition (in the part of the time when the oxygen is added), the oxygen concentration in the liquid phase, wherein the ligno-cellulosic material is present during the enzymatic hydrolysis, is preferably at most 80% of the saturation concentration of oxygen under the hydrolysis reaction conditions, more preferably at most $0.12$ mol/m$^3$, still more preferably at most $0.09$ mol/m$^3$, even more preferably at most $0.06$ mol/m$^3$, even still more preferably at most $0.045$ mol/m$^3$ and most preferably at most $0.03$ mol/m$^3$. Temperature and pressure will influence the DO. The preferred and exemplary mol/m$^3$ values given above relate to normal atmospheric pressure and a temperature of about 62° C. The skilled person in the art will appreciate favourable DO values on basis of the present teachings.

According to another preferred embodiment of the invention the reactor for the enzymatic hydrolysis has a volume of 1 m³ or more. The enzymatic hydrolysis time of the present process is preferably from 5 to 150 hours. According to a further preferred aspect of the invention the enzyme composition is derived from a fungus, preferably a microorganism of the genus *Rasamsonia* or the enzyme composition comprises a fungal enzyme, preferably a *Rasamsonia* enzyme. According to a still further preferred aspect of the invention the dry matter content in the hydrolysis step c) is 10 wt % or more, preferably 14 wt % or more and still more preferably from 14 to 33% wt %. The enzymatic hydrolysis preferably takes place in a batch, fed batch and/or continuous culture reactor. Preferably the oxygen that is introduced in the present process is an oxygen-containing gas such as air. By less oxygen is added to or is present in to the ligno-cellulosic material during part of the time of the enzymatic hydrolysis, is meant that at least 50% less, preferably at least 70% less, most preferably at least 90% less of oxygen (expressed in mol oxygen/m³) is introduced, for example in bubble-form or is present than is added or is present during to the other part of the time of the enzymatic hydrolysis wherein less oxygen is added.

In a preferred embodiment the oxygen is added in the form of (gaseous) bubbles.

Surprisingly, according to the invention, by the addition of oxygen it is possible to attain many process advantages, including optimal temperature conditions, reduced process time, reduced dosage of enzyme, re-use of enzymes, higher yields and other process optimizations, resulting in reduced costs.

In an embodiment the stable enzyme composition used retains activity for 30 hours or more. According to a further embodiment the hydrolysis is preferably conducted at a temperature of 45° C. or more, preferably at a temperature of 50° C. or more and more preferably at a temperature of 55° C. or more. The process of the invention will be illustrated in more detail below.

DETAILED DESCRIPTION OF A PREFERRED EMBODIMENT

Figure 1:
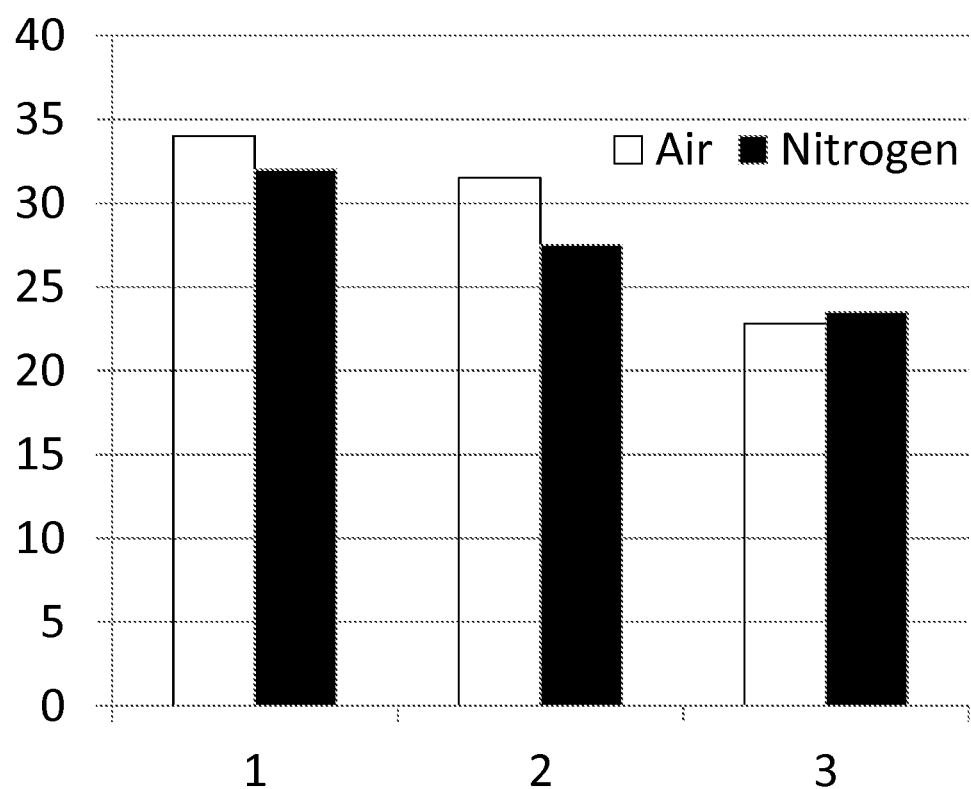
FIG. 1: The effect of sparging nitrogen or air through a 10% aCS feedstock before hydrolysis, on the total amount of glucose (g/l) released by the TEC-210 mix (1), 4E-GH61 mix (2) and 4E-EG mix (3).

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

In the context of the present invention "improved", "increased", "reduced" is used to indicate that the present invention shows an advantage compared to the same situation, process or process conditions except that no extra oxygen is added. Within the context of the present invention "measured under the same conditions" or "analysed under the same conditions" etc. means that the process of the invention and the same process without (or with less) addition of oxygen are performed under the same conditions (except the oxygen addition) and that the results of the present process, if compared to the process without (or with less) oxygen addition, are measured using the same conditions, preferably by using the same assay and/or methodology, more preferably within the same or parallel experiment. Conditions of the hydrolysis are an example of such conditions.

In prior art it is suggested to improve the hydrolysis of cellulolytic material by using anaerobic (WO2010/080407) or vacuum (WO2009/046538) conditions during the enzymatic hydrolysis. In the processes of both documents the oxygen level was decreased. It has been surprisingly found that the hydrolysis of the present invention shows results in an improved reaction product that gives higher amounts of (reduced) sugar products and/or desired fermentation products in the fermentation following the hydrolysis as compared to a process wherein no oxygen is added. In general an increase of the glucose conversion is observed of 5 to 15 w/w %, or even up to 25 w/w %.

Oxygen can be added in several ways. For example oxygen can be added as oxygen gas, oxygen enriched gas such as oxygen enriched air or air (example of oxygen containing gas). Oxygen can be added continuously or dis-continuously. By oxygen "is added" is meant that oxygen is added to the liquid phase (comprising the ligno-cellulosic material) in the hydrolysis reactor and not that oxygen is present in the headspace in the reactor above the liquid phase (in combination with slow or no stirring) whereby the oxygen has to diffuse from the headspace to the liquid phase. So preferably the oxygen is added as bubbles, most preferably as small bubbles.

In case the enzyme may be damaged by the presence or addition of oxygen, milder oxygen supply may be used. In that case a balance can be found between the improved glucose production and the enzyme performance. The addition of the oxygen to the cellulolytic material can be done during the enzymatic hydrolysis. In case oxygen is added in gaseous form, oxygen-containing gas can be introduced, for example blown, into the liquid hydrolysis reactor contents of cellulolytic material. In another embodiment of invention the oxygen-containing gas is introduced into the liquid cellulolytic material stream that will enter the hydrolysis reactor. In still another embodiment of the invention the oxygen containing gas is introduced together with the cellulolytic material that enters the hydrolysis reactor or with part of the liquid reactor contents that passes an external loop of the reactor. In most cases the addition of oxygen before entering the hydrolysis reactor is not sufficient enough and oxygen addition may be done during the hydrolysis as well. In another embodiment of the invention the gaseous phase present in the upper part of the reactor (head space) is continuously or dis-continuously refreshed with the oxygen-containing gas. In the latter case (vigorous) mixing or stirring is needed to get the oxygen as bubbles and/or by diffusion into the liquid reactor contents preferably in combination with over-pressure in the reactor. In general flushing the headspace with air in combination with (vigorous) mixing or stirring may introduce sufficient oxygen into the cellulosic material in the hydrolysis reactor for reactors up to a size of 100 liter to 1 m$^3$. At larger scale, for example in a reactor of 50 m$^3$ or more, for example 100 m$^3$, so much energy is needed for vigorous stirring that from economic point of view this will not be applied in a commercially operating process.

According to the present invention the oxygen may be added before the hydrolysis step, during part of the hydrolysis step, during the whole hydrolysis step or a combination of before or during the hydrolysis step. Advantageously the oxygen is added during part of the hydrolysis step. The addition of oxygen during only part of the hydrolysis may be done for example in case of oxidation damage of the enzyme(s) occurs. In case the oxygen present in the hydrolysis reactor contents or the sugar product or hydrolysate formed in the hydrolysis step might influence or disturb in the subsequent fermentation step, oxygen addition may be done except for the last part of the hydrolysis and thus (most of) the oxygen is consumed before the hydrolysed biomass enters the fermentation reactor. Advantageously the oxygen, preferably in the form of (gaseous) bubbles, is added in the last part of the hydrolysis step.

The inventors pose the hypothesis that in the first part of the (enzymatic) hydrolysis (step) amorphous polysaccharides are hydrolysed to sugars such as glucose and that in the second part of the hydrolysis step the remaining crystalline polysaccharides are converted to sugars. Amorphous polysaccharides are for example converted to oligosaccharides by endogluconases whereafter the oligosaccharides can be converted by cellobiohydrolase and beta-glucosidase (BG) to sugars. According to the present hypothesis amorphous polysaccharides are located on the outside of polysaccharides or polysaccharide complexes whereas crystalline polysaccharides are located relatively more in the inside of the polysaccharides or polysaccharide complexes present in the ligno-cellulosic material. So the conversion of the crystalline polysaccharides may continue even when most of the amorphous polypeptides are hydrolysed. Especially the addition of oxygen is beneficial during the hydrolysis of the crystalline polysaccharides for example in the degradation of the polysaccharides into oligosaccharides. According to this hypothesis oxygen addition is especially useful in the second part of the hydrolysis step. In general, a shorter time of oxygen addition (or shorter second part of hydrolysis) is needed in case of relatively low amounts of crystalline polysaccharides in the ligno-cellulosic material compared hydrolysis of ligno-cellulosic material in which relatively higher amounts of crystalline polysaccharides are present. The inventors also pose that the addition of oxygen is beneficial for the hydrolysis of crystalline polysaccharides. Therefore the addition of oxygen is very useful especially in the phase wherein crystalline polysaccharides are attacked by enzymes. Outside this phase not adding of oxygen might be more efficient. Therefore the oxygen supply may start only in the second part or second half of the hydrolysis. At the end of the hydrolysis when most of the crystalline polysaccharides are degraded, the oxygen addition is preferably stopped. In the last part of the second part or second half of the hydrolysis, most of the polysaccharides are converted to oligosaccharides which during further breakdown to smaller sugars do not need oxygen anymore. Therefore preferably less oxygen, compared to the oxygen addition during the aerated part of the time, is added to the ligno-cellulosic material at the end of the hydrolysis process or more preferably no oxygen is added to the ligno-cellulosic material at the end of the hydrolysis process. This hypothesis is only given as possible explanation of the effect noticed by the inventors and the present invention does not fall or stand with the correctness of this theory.

The inventors have also noticed that aeration during an enzymatic hydrolysis process in the beginning of the hydrolysis process results in an increased glucose production during the hydrolysis.

Figure 3:
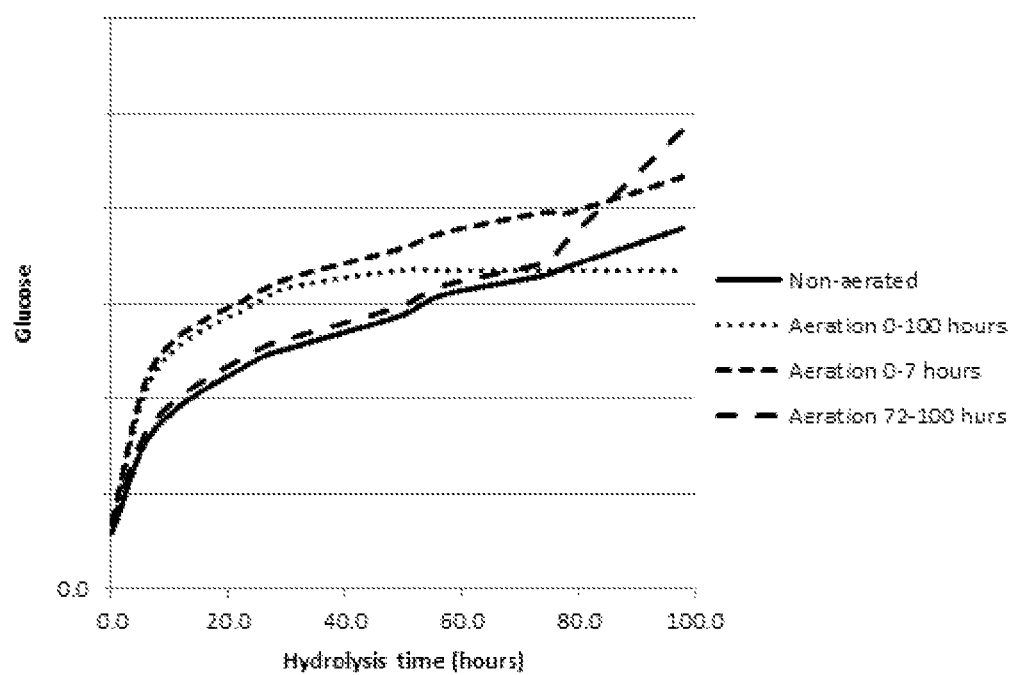
FIG. 3: The effect of time of aeration on glucose produced during enzymatic hydrolysis, —— =no aeration, ●●●=aeration between hydrolysis time is 0 and 100 hours, - - - aeration between hydrolysis-time is 0 and 7 hours and — — — = =aeration between hydrolysis-time is 72 and 100 hours

In FIG. 3 the effect of aeration is shown. Compared to the non-aerated hydrolysis (shown as "non-aerated" curve), an aeration at the start of the hydrolysis process (shown as "aeration 0-7 hours" curve) will result in an immediate increase in glucose production and for example already after 24 hours of hydrolysis a glucose production will be found that corresponds to a glucose production without aeration of 60 hours hydrolysis under identical conditions (except for aeration). Compared to the non-aerated hydrolysis, an aeration at the last part of the hydrolysis process (shown as "aeration 72-100 hours" curve) will result in an immediate increase in glucose production after aeration and for example already after 24 hours after the start of aeration (at 72 hours) in the hydrolysis process a glucose production increase of 30% will be found compared to the glucose production without aeration under identical conditions (except for aeration). It is believed by the inventors that by using an aeration at the start as well as at the last part of the hydrolysis process (with in between the aeration intervals a period of no aeration) might increase glucose production whereby this results in an increase of glucose production that is larger than one of the two separate increases. The present explanation is given to guide and instruct the skilled person in the art to select the proper conditions for the present hydrolysis process.

Several examples of (partial) aeration during the enzymatic hydrolysis process are given in the Examples to show the beneficial effect of the present invention. This beneficial effect is found for several substrates or feedstocks and therefore believed to be present for the hydrolysis of all kind of substrates or feedstocks.

Several examples of enzyme compositions for the enzymatic hydrolysis process are given in the Examples to show the beneficial effect of the present invention. This beneficial effect is found for several enzyme compositions and therefore believed to be present for all kind of hydrolysing enzyme compositions.

According to a preferred embodiment of the invention the part of the time wherein less or preferably no oxygen is added is 10 to 80%, preferably 20 to 80%, more preferably 30 to 80% and most preferably 40 to 80% of the total enzymatic hydrolysis time. According to a further preferred embodiment of the invention the part of the time wherein more oxygen is added is 2 to 80%, preferably 4 to 60%, more preferably 8 to 50% and most preferably 10 to 50% of the total enzymatic hydrolysis time. In general the oxygen concentration in the liquid phase during the part of the time wherein oxygen is added is at least 2 times, preferably at least 4 times, more preferably at least 10 times the oxygen concentration in the liquid phase during the part of the time wherein less or no oxygen is added.

To a further preferred embodiment of the invention during the part of the time wherein oxygen addition takes place in the liquid phase (by aeration or addition of oxygen), the oxygen concentration (DO) in the liquid phase wherein the ligno-cellulosic material is present during the enzymatic hydrolysis, is at least 0.001 mol/m$^3$, preferably at least 0.002 mol/m$^3$, more preferably at least 0.003 mol/m$^3$ and even more preferably more than 0.01 mol/m$^3$, for example more than 0.02 mol/m$^3$ or 0.03 mol/m$^3$. In reactors of less than 1 m$^3$ DO values of below 0.01 mol/m$^3$ or 0.02 mol/m$^3$ will be obtained by slow stirring. Vigorous mixing or stirring at such scale introduces part of the gas phase of the headspace into the reaction liquid. For example the mixing or stirring may create a whirlpool that draws oxygen into the liquid. In general flushing the headspace with oxygen (for example in the form of air) in combination with (vigorous) mixing or stirring will introduce sufficient oxygen into the cellulosic material in the hydrolysis reactor for reactors up to a size of 100 liter to 1 m$^3$. At larger scale, for example in a reactor of 50 m$^3$ or more, for example 100 m$^3$, so much energy is needed for vigorous stirring that from economic point of view this will not be applied in a commercially operating process. In general in large reactors, stirring or mixing without introducing air or oxygen will result in DO values of less than 0.01 mol/m$^3$.

To still another preferred embodiment of the invention during the oxygen generation or production the oxygen concentration in the liquid phase (aeration or addition of oxygen), the oxygen concentration in the liquid phase wherein the ligno-cellulosic material is present during the enzymatic hydrolysis, is during the part of the time wherein oxygen is added preferably at most 80% of the saturation concentration of oxygen under the hydrolysis reaction conditions, more preferably at most 0.12 mol/m$^3$, still more preferably at most 0.09 mol/m$^3$, even more preferably at most 0.06 mol/m$^3$, even still more preferably at most 0.045 mol/m$^3$ and most preferably at most 0.03 mol/m$^3$. Temperature and pressure will influence the DO. The preferred and exemplary mol/m$^3$ values given above relate to normal atmospheric pressure and a temperature of about 62° C. The skilled person in the art will appreciate favourable DO values on basis of the present teachings.

To a further preferred embodiment of the invention the oxygen concentration in the liquid phase, wherein the ligno-cellulosic material is present during the enzymatic hydrolysis, is during the part of the time wherein less or no oxygen is added less than 0.02 mol/m$^3$, preferably less than 0.01 mol/m$^3$, more preferably less than 0.005 mol/m$^3$, and most preferably less than 0.001 mol/m$^3$.

The oxygen addition in the form of air or other oxygen-containing gas according to the invention may also be used to at least partially stir or mix the hydrolysis reactor contents. The present process of the invention shows especially on pilot plant and industrial scale advantages. Preferably the hydrolysis reactor has a volume of 1 m$^3$ or more, preferably of more than 10 m$^3$ and most preferably of 50 m$^3$ or more. In general the hydrolysis reactor will be smaller than 3000 m$^3$ or 5000 m$^3$ The inventors pose the theory that especially at large scale insufficient oxygen is available for the hydrolysis which might be due to oxygen transfer limitations in the reactor for example in the cellulolytic biomass. On lab-scale experiments this oxygen-insufficiency may play a less important role. The surface area (or oxygen contact area of the reactor content) to reactor volume ratio is more favourable for small scale experiments than in large scale experiments. Moreover mixing in small scale experiments is relatively easier than at large scale. During those small scale experiments also the transport of oxygen from the headspace of the hydrolysis reactor is faster than compared to the situation in large scale experiments. This theory is only given as possible explanation of the effect noticed by the inventors, and the present invention does not fall or stands with the correctness of this theory. According to a further embodiment of the invention the addition of oxygen may be used to control at least partially the hydrolysis process.

On large scale (for example in a reactor having a volume of more than 1 m$^3$ it was noticed that the oxygen addition resulted in improved hydrolysis and/or a faster hydrolysis. Moreover the inventors were able to further improve the hydrolysis process by using smaller amounts of enzymes (on protein) and still obtaining high hydrolysis levels. One of the major costs of the hydrolysis is the cost of the enzyme or enzyme composition. Therefore reducing the amount of enzymes needed is an enormous economic advantage.

The process of the present invention makes it possible to use amounts of enzyme (or enzyme composition) of less than 7.5 mg enzyme/g glucan, preferably less than 6.0 mg enzyme/g glucan, more preferably less than 5.0 mg glucan/g feedstock, still more preferably less than 4.0 mg enzyme/g glucan and most preferably less than 2.5 mg enzyme/g glucan (on dry matter and enzyme as protein).

The glucan content of acid treated feedstock is about 25 to 50 wt % (dry matter). For corn stover the glucan content is about 30 to 45 wt % (dry matter).

Therefore in general amounts of enzyme (or enzyme composition) of between 0.1 and 7.5 mg enzyme/g glucan, preferably between 0.2 and 7.5 mg enzyme/g glucan, more preferably of between 0.2 and 6.0 mg enzyme/g glucan, even more preferably of between 0.2 and 5.0 mg enzyme/g glucan, still more preferably of between 0.2 and 4.0 mg enzyme/g glucan and most preferably of between 0.2 and 2.5 mg enzyme/g glucan (on dry matter and enzyme as protein) will be used in the process of the invention.

The process of the present invention makes it possible to use amounts of enzyme (or enzyme composition) of less than 3.0 mg enzyme/g feedstock, preferably less than 2.5 mg enzyme/g feedstock, more preferably less than 2.0 mg enzyme/g feedstock, still more preferably less than 1.5 mg enzyme/g feedstock and most preferably less than 1.0 mg enzyme/g feedstock (on dry matter and enzyme as protein).

In general amounts of enzyme (or enzyme composition) of between 0.05 and 3.0 mg enzyme/g feedstock, preferably between 0.1 and 3.0 mg enzyme/g feedstock, more preferably of between 0.1 and 2.5 mg enzyme/g feedstock, even more preferably of between 0.1 and 2.0 mg enzyme/g feedstock, still more preferably of between 0.1 and 1.5 mg enzyme/g feedstock and most preferably of between 0.1 and 1.0 mg enzyme/g feedstock (on dry matter and enzyme as protein) will be used in the process of the invention.

By using these amounts of enzyme (or enzyme composition), a glucan conversion level of more 70% can be obtained, preferably more than 72%. In general glucan conversion levels of between 70% and 90% can be obtained, preferably levels of between 72% and 90% and even more preferably levels of between 74% and 90%. The glucan conversion level determination is described in the Examples.

The process of the invention is advantageously applied in combination with the use of thermostable enzymes.

A "thermostable" enzyme means that the enzyme has a temperature optimum 60° C. or higher, for example 70° C. or higher, such as 75° C. or higher, for example 80° C. or higher such as 85° C. or higher. They may for example be isolated from thermophilic microorganisms, or may be designed by the skilled person and artificially synthesized. In one embodiment the polynucleotides may be isolated or obtained from thermophilic or thermotolerant filamentous fungi or isolated from non-thermophilic or non-thermotolerant fungi but are found to be thermostable.

By "thermophilic fungus" is meant a fungus that grows at a temperature of 50° C. or above. By "themotolerant" fungus is meant a fungus that grows at a temperature of 45° C. or above, having a maximum near 50° C.

Examples of thermophilic fungal strains are *Rasamsonia emersonii* (formerly known as *Talaromyces emersoni ; Talaromyces emersonii, Penicillium geosmithia emersonii* and *Rasamsonia emersonii* are used interchangeably herein).

Suitable thermophilic or thermotolerant fungal cells may be a *Humicola, Rhizomucor, Myceliophthora, Rasamsonia, Talaromyces, Thermomyces, Thermoascus* or *Thielavia* cell, preferably a *Rasamsonia emersonii* cell. Preferred thermophilic or thermotolerant fungi are *Humicola grisea* var. *thermoidea, Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces, Thermomyces* and *Thermoascus* in the Eurotiales (Mouchacca 1997). The majority of *Talaromyces* species are mesophiles but exceptions are species within sections *Emersonii* and *Thermophila*. Section *Emersonii* includes *Talaromyces emersonii, Talaromyces byssochlamydoides, Talaromyces bacillisporus* and *Talaromyces leycettanus*, all of which grow well at 40° C. *Talaromyces bacillisporus* is thermotolerant, *T. leycettanus* is thermotolerant to thermophilic, and *T. emersonii* and *T. byssochlamydoides* are truly thermophilic (Stolk and Samson 1972). The sole member of *Talaromyces* section *Thermophila, T. thermophilus*, grows rapidly at 50° C. (Evans and Stolk 1971; Evans 1971; Stolk and Samson 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*T. byssochlamydoides* and *T. leycettanus*) or *Penicillium cylindrosporum* series (*T. emersonii* and *T. bacillisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *G. argillacea* is thermotolerant, and Stolk et al. (1969) and Evans (1971) proposed a connection with members of *Talaromyces* sect. *Emersonii*. The phylogenetic relationship of the themophilic *Talaromyces* species within *Talaromyces* and the *Trichocomaceae* is unknown. See J. Houbraken, Antonie van Leeuwenhoek 2012 Feb.; 101(2): 403-21.

*Rasamsonia* is a new genus comprising thermotolerant and thermophilic *Talaromyces* and *Geosmithia* species (J. Houbraken et al *vida supra*). Based on phenotypic, physiological and molecular data, Houbraken et al proposed to transfer the species *T. emersonii, T. byssochlamydoides, T. eburneus, G. argillacea* and *G. cylindrospora* to *Rasamsonia* gen. nov. *Talaromyces emersonii, Penicillium geosmithia emersonii* and *Rasamsonia emersonii* are used interchangeably herein.

Preferred thermophilic fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*.

"Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Panerochaete, Pleurotus, Rasamsonia, Schizophyllum, Talaromyces, Thermoascus, Thermomyces, Thielavia, Tolypocladium*, and *Trichoderma*.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

An advantage of expression and production of the enzymes (for example at least two, three or four different cellulases) in a suitable microorganism may be a high enzyme composition yield which can be used in the process of the present invention.

According to the invention, by the addition of oxygen it is possible to attain many process advantages, including optimal temperature conditions, reduced process time, reduced dosage of enzyme, re-use of enzymes and other process optimizations, resulting in reduced costs. Advantageously the invention provides a process in which the hydrolysis step is conducted at improved conditions. The invention also provides a process involving hydrolysis having a reduced process time. Furthermore the invention provides a process, wherein the dosage of enzyme may be reduced and at the same time output of useful hydrolysis product is maintained at the same level. Another advantage of the invention is that the present process involving hydrolysis may result in process conditions which are optimized. A still further advantage of the invention is that the output of useful hydrolysis product of the process involving hydrolysis is increased using the same enzyme dosage.

Stable Enzyme Composition

Stable enzyme composition herein means that the enzyme composition retains activity after 30 hours of hydrolysis reaction time, preferably at least 10%, 20%, 30%, 40%, 50%, 60%, 65%, 70%, 75%, 80%, 85%, 90%, 95%, 96%, 97%, 98%, 99%, or 100% of its initial activity after 30 hours of hydrolysis reaction time. Preferably the enzyme composition retains activity after 40, 50, 60, 70, 80, 90 100, 150, 200, 250, 300, 350, 400, 450, 500 hours of hydrolysis reaction time.

The enzyme composition may be prepared by fermentation of a suitable substrate with a suitable microorganism, e.g. *Rasamsonia emersonii* or *Aspergillus niger* wherein the enzyme composition is produced by the microorganism. The microorganism may be altered to improve or to make the cellulase composition. For example the microorganism may be mutated by classical strain improvement procedures or by recombinant DNA techniques. Therefore the microorganisms mentioned herein can be used as such to produce the cellulase composition or may be altered to increase the production or to produce an altered cellulase composition which might include heterologous cellulases, thus enzymes that are not originally produced by that microorganism. Preferably a fungus, more preferably a filamentous fungus is used to produce the cellulase composition. Advantageously a thermophilic or thermotolerant microorganism is used. Optionally a substrate is used that induces the expression of the enzymes in the enzyme composition during the production of the enzyme composition.

The enzyme composition is used to release sugars from lignocellulose, that comprises polysaccharides. The major polysaccharides are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert. By sugar product is meant the enzymatic hydrolysis product of the feedstock or ligno-cellulosic material. The sugar product will comprise soluble sugars, including both monomers and multimers, preferably will comprise glucose. Examples of other sugars are cellobiose, xylose, arabinose, galactose, fructose, mannose, rhamnose, ribose, galacturonic acid, glucoronic acid and other hexoses and pentoses. The sugar product may be used as such or may be further processed for example purified.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Enzymes that may be included in the stable enzyme composition used in the invention are now described in more detail:

GH61, Endoglucanases (EG) and exo-cellobiohydrolases (CBH) catalyze the hydrolysis of insoluble cellulose to products such as cellooligosaccharides (cellobiose as a main product), while β-glucosidases (BG) convert the oligosaccharides, mainly cellobiose and cellotriose to glucose.

Hemicellulose is a complex polymer, and its composition often varies widely from organism to organism and from one tissue type to another. In general, a main component of hemicellulose is β-1,4-linked xylose, a five carbon sugar. However, this xylose is often branched at 0 to 3 and/or 0 to 2 atom of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

A composition for use in a method of the invention comprises preferably at least two activities, although typically a composition will comprise more than two activities, for example, three, four, five, six, seven, eight, nine or more. Typically, a composition of the invention may comprise at least two different celulases or one cellulase and at least one hemicellulase. A composition of the invention may comprise cellulases, but no xylanases. In addition, a composition of the invention may comprise auxiliary enzyme activity, i.e. additional activity which, either directly or indirectly leads to lignocellulose degradation. Examples of such auxiliary activities are mentioned herein.

Thus, a composition for use in the invention may comprise GH61, endoglucanase activity and/or cellobiohydrolase activity and/or β-glucosidase activity. A composition for use in the invention may comprise more than one enzyme activity in one or more of those classes. For example, a composition for use in the invention may comprise two endoglucanase activities, for example, endo-1,3(1,4)-β glucanase activity and endo-β-1,4-glucanase activity. Such a composition may also comprise one or more xylanase activities. Such a composition may comprise an auxiliary enzyme activity.

A composition for use in the invention may be derived from *Rasamsonia emersonii*. In the invention, it is anticipated that a core set of (lignocellulose degrading) enzyme activities may be derived from *Rasamsonia emersonii*. *Rasamsonia emersonii* can provide a highly effective set of activities as demonstrated herein for the hydrolysis of lignocellulosic biomass. That activity can then be supplemented with additional enzyme activities from other sources. Such additional activities may be derived from classical sources and/or produced by a genetically modified organism.

The activities in a composition for use in the invention may be thermostable. Herein, this means that the activity has a temperature optimum of about 60° C. or higher, for example about 70° C. or higher, such as about 75° C. or higher, for example about 80° C. or higher such as 85° C. or higher. Activities in a composition for use in the invention will typically not have the same temperature optima, but preferably will, nevertheless, be thermostable.

In addition, enzyme activities in a composition for use in the invention may be able to work at low pH. For the purposes of this invention, low pH indicates a pH of about 5.5 or lower, about 5 or lower, about 4.9 or lower, about 4.8 or lower, about 4.7 or lower, about 4,6 or lower, about 4.5 or lower, about 4.4 or lower, about 4.3 or lower, about 4.2 or lower, about 4,1 or lower, about 4.0 or lower about 3.9 or lower, or about 3.8 or lower, about 3.7 or lower, about 3.6 or lower, or about 3.5 or lower.

Activities in a composition for use in the invention may be defined by a combination of any of the above temperature optima and pH values.

The composition used in a method of the invention may comprise, in addition to the activities derived from *Rasamsonia*, a cellulase (for example one derived from a source other than *Rasamsonia*) and/or a hemicellulase (for example one derived from a source other than *Rasamsonia*) and/or a pectinase.

A composition for use in the invention may comprise one, two, three, four classes or more of cellulase, for example one, two three or four or all of a GH61, an endoglucanase (EG), one or two exo-cellobiohydrolase (CBH) and a β-glucosidase (BG). A composition for use in the invention may comprise two or more of any of these classes of cellulase.

A composition of the invention may comprise an activity which has a different type of cellulase activity and/or hemicellulase activity and/or pectinase activity than that provided by the composition for use in a method of the invention. For example, a composition of the invention may comprise one type of cellulase and/or hemicellulase activity and/or pectinase activity provided by a composition as described herein and a second type of cellulase and/or hemicellulase activity and/or pectinase activity provided by an additional cellulose/hemicellulase/pectinase.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

GH61 (glycoside hydrolase family 61 or sometimes referred to EGIV) proteins are oxygen-dependent polysaccharide monooxygenases (PMO's) according to the latest literature. Often in literature these proteins are mentioned to enhance the action of cellulases on lignocellulose substrates. GH61 was originally classified as endogluconase based on measurement of very weak endo-1,4-β-d-glucanase activity in one family member. The term "GH61" as used herein, is to be understood as a family of enzymes, which share common conserved sequence portions and foldings to be classified in family 61 of the well-established CAZY GH classification system (http://www.cazy.org/GH61.html). The glycoside hydrolase family 61 is a member of the family of glycoside hydrolases EC 3.2.1. GH61 is used herein as being part of the cellulases.

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a GH61, a cellobiohydrolase, an endo-β-1,4-glucanase, a β-glucosidase or a β-3-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D- xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3-or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3-or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A composition of the invention may comprise any hemicellulase, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)-and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: $(1,4-\alpha-D-galacturonide)_n+H_2O= (1,4-\alpha-D-galacturonide)_{n-1}+D-galacturonate$. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→44)-α-D-galacturonan reducing-end-disaccharide-lyase.

Herein, rhamnogalacturonan hydrolase is any polypeptide which is capable of hydrolyzing the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)-and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a GH61, a cellobiohydrolase, an endoglucanase and/or a β-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase or an expansin or a cellulose induced protein or a cellulose integrating protein or like protein may be present in a composition of the invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the invention may be a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition for use in a method of the invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in a method of the invention may be composed of enzymes from (1) commercial suppliers; (2) cloned genes expressing enzymes; (3) complex broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover or wheat straw), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses (pre-treated) feedstock (such as corn stover or wheat straw) to provide nutrition to an organism that produces an enzyme(s). In this manner, plants that produce the enzymes may themselves serve as a lignocellulosic feedstock and be added into lignocellulosic feedstock.

In the uses and methods described herein, the components of the compositions described above may be provided concomitantly (i.e. as a single composition per se) or separately or sequentially.

The invention thus relates to methods in which the composition described above are used and to uses of the composition in industrial processes.

Ligno-cellulosic Material

Lignocellulosic material herein includes any lignocellulosic and/or hemicellulosic material. Lignocellulosic material suitable for use as feedstock in the invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, switch grass, miscanthus, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Pre-treatment

The feedstock may optionally be pre-treated with heat, mechanical and/or chemical modification or any combination of such methods in order to to enhance the accessibility of the substrate to enzymatic hydrolysis and/or hydrolyse the hemicellulose and/or solubilize the hemicellulose and/or cellulose and/or lignin, in any way known in the art. In one embodiment, the pre-treatment is conducted treating the lignocellulose with steam explosion, hot water treatment or treatment with dilute acid or dilute base.

Washing Step

Optionally, the process according to the invention comprises a washing step. The optional washing step may be used to remove water soluble compounds that may act as inhibitors for the fermentation step. The washing step may be conducted in known manner.

Enzymatic Hydrolysis

The enzyme composition used in the process of the invention can extremely effectively hydrolyze lignocellulolytic material, for example corn stover or wheat straw, which can then be further converted into a useful product, such as ethanol, biogas, butanol, lactic acid, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials. The present invention is exemplified with the production of ethanol but this is done as exemplification only rather than as limitation, the other mentioned useful products can be produced equally well.

The process according to the invention comprises an enzymatic hydrolysis step. The enzymatic hydrolysis includes, but is not limited to, hydrolysis for the purpose of liquification of the feedstock and hydrolysis for the purpose of releasing sugar from the feedstock or both. In this step optionally pre-treated and optionally washed ligno-cellulosic material is brought into contact with the enzyme composition according to the invention. Depending on the lignocellulosic material and the pre-treatment, the different reaction conditions, e.g. temperature, enzyme dosage, hydrolysis reaction time and dry matter concentration, may be adapted by the skilled person in order to achieve a desired conversion of lignocellulose to sugar. Some indications are given hereafter.

In one aspect of the invention the hydrolysis is conducted at a temperature of 45° C. or more, of 50° C. or more, 55° C. or more, 60° C. or more, 65° C. or more, or 70° C. or more. The high temperature during hydrolysis has many advantages, which include working at the optimum temperature of the enzyme composition, the reduction of risk of (bacterial) contamination, reduced viscosity, smaller amount of cooling water required, use of cooling water with a higher temperature, re-use of the enzymes and more.

In a further aspect of the invention, the amount of enzyme composition added (herein also called enzyme dosage or enzyme load) is low. In an embodiment the amount of enzyme is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). Low enzyme dosage is possible, since because of the activity and stability of the enzymes, it is possible to increase the hydrolysis reaction time.

In a further aspect of the invention, the hydrolysis reaction time is 5 hours or more, 10 hours or more, 20 hours or more, 40 hours or more, 50 hours or more, 60 hours or more, 70 hours or more, 80 hours or more, 90 hours or more, 100 hours or more, 120 hours or more, 130 h or more. In another aspect, the hydrolysis reaction time is 5 to 150 hours, 40 to 130 hours, 50 to 120 hours, 60 to 120 hours, 60 to 110 hours, 60 to 100 hours, 70 to 100 hours, 70 to 90 hours or 70 to 80 hours. Due to the stability of the enzyme composition longer hydrolysis reaction times are possible with corresponding higher sugar yields.

The pH during hydrolysis may be chosen by the skilled person. In a further aspect of the invention, the pH during the hydrolysis may be 3.0 to 6.4. The stable enzymes of the invention may have a broad pH range of up to 2 pH units, up to 3 pH units, up to 5 pH units. The optimum pH may lie within the limits of pH 2.0 to 8.0, 3.0 to 8.0, 3.5 to 7.0, 3.5 to 6.0, 3.5 to 5.0, 3.5 to 4.5, 4.0 to 4.5 or is about 4.2.

In a further aspect of the invention the hydrolysis step is conducted until 70% or more, 80% or more, 85% or more, 90% or more, 92% or more, 95% or more of available sugar in lignocellulosic material is released.

Significantly, a process of the invention may be carried out using high levels of dry matter (of the lignocellulosic material) in the hydrolysis reaction. Thus, the invention may be carried out with a dry matter content of about 5 wt % or higher, about 8 wt % or higher, about 10 wt % or higher, about 11 wt % or higher, about 12 wt % or higher, about 13 wt % or higher, about 14 wt % or higher, about 15 wt % or higher, about 20 wt % or higher, about 25 wt % or higher, about 30 wt % or higher, about 35 wt % or higher or about 40 wt % or higher. In a further embodiment, the dry matter content in the hydrolysis step is 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt % or more or 14 to 33 wt %.

Fermentation

The process according to the invention comprises a fermentation step. In a further aspect, the invention thus includes in step fermentation processes in which a microorganism is used for the fermentation of a carbon source comprising sugar(s), e.g. glucose, L-arabinose and/or xylose. The carbon source may include any carbohydrate oligo-or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic feedstock (e.g. 50 g/l xylose, 35 g/l L-arabinose and 10 g/l galactose. For more dilute sugar compositions the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

In an embodiment of the invention, in step the fermentation is conducted with a microorganism that is able to ferment at least one C5 sugar. In an embodiment the process is a process for the production of ethanol whereby the process comprises the step comprises fermenting a medium containing sugar(s) with a microorganism that is able to ferment at least one C5 sugar, whereby the host cell is able to ferment glucose, L-arabinose and xylose to ethanol. In an embodiment thereof the microorganism that is able to ferment at least one C5 sugar is a yeast. In an embodiment, the yeast is belongs to the genus *Saccharomyces*, preferably of the species *Saccharomyces cerevisiae*, in which genetic modifications have been made. An example of such a microorganism and its preparation is described in more detail in WO 2008/041840 and in European Patent Application EP10160622.6, filed 21 Apr. 2010. In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

In such process, the volumetric ethanol productivity is preferably at least 0.5, 1.0, 1.5, 2.0, 2.5, 3.0, 5.0 or 10.0 g ethanol per liter per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g. ethanol per g. glucose or xylose.

In one aspect, the fermentation process leading to the production of ethanol, has several advantages by comparison to known ethanol fermentations processes:
  anaerobic processes are possible;
  oxygen limited conditions are also possible;
  higher ethanol yields and ethanol production rates can be obtained;
  the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobical or anaerobical conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the composition of the invention is capable of acting at low pH and, therefore, there is no need to adjust the pH of acid of an acid pretreated feedstock in order that saccharification or hydrolysis may take place. Accordingly, a method of the invention may be a zero waste method using only organic products with no requirement for inorganic chemical input.

Overall Reaction Time

According to the invention, the overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly lower overall times may be reached at lower glucose yield.

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including biogas, ethanol and butanol); lactic acid; 3-hydroxy-propionic acid; acrylic acid; acetic acid; 1,3-propane-diol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

Separation of Fermentation Product

The process according to the invention optionally comprises recovery of fermentation product. A fermentation product may be separated from the fermentation broth in any known manner. For each fermentation product the skilled person will thus be able to select a proper separation technique. For instance ethanol may be separated from a yeast fermentation broth by distillation, for instance steam distillation/vacuum distillation in conventional way.

Certain embodiments of the invention will below be described in more detail, but are in no way limiting the scope of the present invention.

Use of Thermostable Enzymes Under Optimal Temperature Conditions

In one embodiment, the invention relates to the use of thermostable enzymes such as cellulolytic enzymes of *Rasamsonia* for the production of reducing sugars from pre-treated ligno-cellulosic feedstock in, but not limiting to, ethanol production. Cellulolytic enzymes of *Rasamsonia* applied on pre-treated ligno-cellulosic feedstock showed maximal conversion rates at temperature within the range of 50 to 70° C. The enzyme remains active under these circumstances for 14 days and more without complete cessation of activity.

By using optimal temperature conditions, maximal amount of reducing sugars can be released from feedstock (total hydrolysis) within the shortest possible hydrolysis time. In this way, 100% conversion of cellulose in glucose is achieved in less than 5 days.

The theoretical maximum yield (Yps max in g product per gram glucose) of a fermentation product can be derived from textbook biochemistry. For ethanol, 1 mole of glucose (180 g) yields according to normal glycolysis fermentation pathway in yeast 2 moles of ethanol (=2×46=92 g ethanol. The theoretical maximum yield of ethanol on glucose is therefore 92/180=0.511 g ethanol/g glucose.

For butanol (MW 74 g/mole) or iso butanol, the theoretical maximum yield is 1 mole of butanol per mole of glucose. So Yps max for (iso-)butanol=74/180=0.411 g (iso-)butanol/g glucose.

For lactic acid the fermentation yield for homolactic fermentation is 2 moles of lactic acid (MW=90 g/mole) per mole of glucose. According to this stoichiometry, the Yps max=1 g lactic acid/g glucose.

For other fermentation products a similar calculation may be made.

The cost reduction achieved with applying cellulolytic enzymes of *Rasamsonia* will be the result of an overall process time reduction.

Compensation of Lower Enzyme Dosage with Extended Hydrolysis Time Using *Rasamsonia* Enzymes Due to the high stability of the stable enzymes, the activities do not cease in time, although less reducing sugars are liberated in the course of the hydrolysis. It is possible to lower the enzyme dosage and extend the use of the enzyme by prolonging the hydrolysis times to obtain similar levels of released reducing sugars. For example, 0.175 mL enzyme/g feedstock dry-matter resulted in release of approximately 90% of the theoretical maximum of reducing sugars from pre-treated feedstock within 72 h. When using 0.075 mL enzyme/g feedstock dry-matter, approximately 90% conversion of the theoretical maximum is achieved within 120 h. The results show that, because of the stability of the enzyme activity, lowering the enzyme dosage can be compensated by extending the hydrolysis time to obtain the same amount of reducing sugars. The same holds for hydrolysis of pre-treated feedstock at dry-matter contents higher than 10% shows that compensating effect of extended hydrolysis time at 15% dry matter feedstock.

The cost reduction achieved by using stable cellulolytic enzymes, such as of *Rasamsonia*, results from requiring less enzyme dosage, resulting in similar hydrolysis conversion yields.

Lowering the Risk on Contamination with Stable Enzymes

In a common process for converting ligno-cellulosic material into ethanol, process steps are preferably done under septic conditions to lower the operational costs. Contamination and growth of contaminating microorganisms can therefore occur and result in undesirable side effects, such lactic acid, formic acid and acetic acid production, yield losses of ethanol on substrate, production of toxins and extracellular polysaccharides, which may affect production costs significantly. A high process temperature and/or a short process time will limit the risk on contamination during hydrolysis and fermentation. Thermostable enzymes, like those of *Rasamsonia*, are capable of hydrolysing ligno-cellulosic feedstock at temperatures of higher than 60° C. At these temperatures, the risk that a contaminating microorganism will cause undesired side effects will be little to almost zero.

During the fermentation step, in which ethanol is produced, temperatures are typically between 30 to 37° C. and will preferably not be raised because of production losses. By applying fermentation process times as short as possible the risks and effects of contamination and/or growth of contaminants will be reduced as much as possible. With stable enzymes, like those of *Rasamsonia* a short as possible fermentation times can be applied (see description above), and thus risks on contamination and/or growth of contaminants will be reduced as much as possible. The cost reduction achieved with applying thermostable cellulolytic enzymes of *Rasamsonia* in this way will result from lower risk of process failures due to contamination.

Stable Enzymes Reduce Cooling Costs and Increase Productivity of Ethanol Plants

The first step after thermal pretreatment will be to cool the pretreated feedstock to temperatures where the enzymes are optimal active. On large scale, this is typically done by adding (cooled) water, which will, besides decreasing the temperature, reduce the dry-matter content. By using thermos stable enzymes, like those of *Rasamsonia,* cost reduction can be achieved by the fact that (i) less cooling of the pretreated feedstock is required since higher temperatures are allowed during hydrolysis, and (ii) less water will be added, which will increase the dry-matter content during hydrolysis and fermentation and thus increase the ethanol production capacity (amount produced per time unit per volume) of an ethanol plant. Also, by using thermostable enzymes according to the invention, like those of *Rasamsonia*, cost reduction may also be achieved by using cooling water having higher temperature that the water that is used in a process with non-thermostable enzyme.

Enzyme Recycling After Hydrolysis with Stable Enzymes

At the end of the hydrolysis, enzyme activities appear to be low since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, sedicantation, etcetera, 60% or more e.g. 70% of the enzyme activity in solution can be recovered and re-used for hydrolysis of a new pre-treated ligno-cellulosic feedstock during the next hydrolysis.

Moreover, after solid-liquid separation the enzyme in solution can be separated from the solution containing reducing sugars and other hydrolysis products from the enzymatic actions. This separation can be done by, but not limiting to, (ultra and micro)filtration, centrifugation, sedicantation, sedimentation, with or without first adsorption of the enzyme to a carrier of any kind.

For example, after hydrolysis of pre-treated feedstock with 0.175 mL/g feedstock dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as of *Rasamsonia*, in this way results from requiring less enzyme dosage.

Enzyme Recycling After Hydrolysis in Combination with Enzyme Production and Yeast-cell Recycling with Stable Enzymes The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme-production fermentation and as substrate for the cultivation of the ethanol-producing microorganism.

Enzyme Recycling After Vacuum Distillation with Stable Enzymes

The thermo stability of enzymes, like those from *Rasamsonia*, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pre-treated wheat straw conversion into ethanol. The thin stillage can be used either in concentrated or (un)diluted form and/or purified and with or without additional enzyme supplementation.

Enzyme Recycling in Combination with Enzyme Supplementation After Vacuum Distillation with Thermostable Enzymes In an optimal process, an amount of enzyme is supplemented into the thin stillage, before its re-use in a new process cycle, equal to the amount of activity lost during the three successive process steps of the previous process cycle. In this way over-dosage of enzyme is avoided and thus most efficient use of enzyme is obtained.

Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

Use of Stable Enzymes in Mixed Systems

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of it in mixed systems is therefore beneficial and will lead to dosage and thus costs reduction.

The invention is further described by the following examples, which should not be construed as limiting the scope of the invention.

EXPERIMENTAL INFORMATION

Strains

*Rasamsonia* (*Talaromyces*) *emersonii* strain was deposited at CENTRAAL BUREAU VOOR SCHIMMELCULTURES, Uppsalalaan 8, P.O. Box 85167, NL-3508 AD Utrecht, The Netherlands in December 1964 having the Accession Number CBS 393.64.

Other suitable strains can be equally used in the present examples to show the effect and advantages of the invention. For example TEC-101, TEC-147, TEC-192, TEC-201 or TEC-210 are suitable *Rasamsonia* strains which are described in WO2011/000949.

Preparation of Acid Pre-treated Corn Stover Substrate.

Dilute-acid pre-treated corn stover (aCS) was obtained as described in Schell, D. J., Applied Biochemistry and Biotechnology (2003), vol. 105-108, pp 69-85. A pilot scale pretreatment reactor was used operating at steady state conditions of 190° C., 1 min residence time and an effective H2SO4 acid concentration of 1.45% (w/w) in the liquid phase.

Protein measurement Assays

1. Total Protein

TCA Biuret

The method was a combination of precipitation of protein using trichloro acetic acid (TCA) to remove disturbing substances and allow determination of the protein concentration with the colorimetric Biuret reaction. In the Biuret reaction, a copper (II) ion is reduced to copper (I), which forms a complex with the nitrogens and carbons of the peptide bonds in an alkaline solution. A violet color indicates the presence of proteins. The intensity of the color, and hence the absorption at 546 nm, is directly proportional to the protein concentration, according to the Beer-Lambert law. The standardisation was performed using BSA (Bovine Serum Albumine) and the protein content was expressed in g protein as BSA equivalent/L or mg protein as BSA equivalent/ml. The protein content was calculated using standard calculation protocols known in the art, by plotting the $OD_{546}$ versus the concentration of samples with known concentration, followed by the calculation of the concentration of the unknown samples using the equation generated from the calibration line.

2. Individual Proteins Using PAGE
Sample Pre-treatment SDS-PAGE

Based on the estimated protein concentration of the samples the following samples preparation was performed. To 10 µl sample 40 µl MilliQ water and 50 µl TCA (20%) was added to dilute the sample five times (~1 mg/ml) and precipitate the proteins. After 1 hour on ice the sample was centrifuged (10 minutes, 14000 rpm). The pellet was washed with 500 µl Aceton and centrifuged (10 minutes, 14000 rpm). The pellet was treated as described below.

SDS-PAGE

The pellet was dissolved in 65 µl of the MilliQ water, 25 µl NuPAGE™ LDS sample buffer (4×) Invitrogen and 10 µl NuPAGE™ Sample Reducing agent (10×) Invitrogen. Prior to the deanuarion step the sample was diluted 5 times using a mix of MilliQ; NuPAGE™ LDS sample buffer and 10 µl NuPAGE™ Sample Reducing in the ratio of 65:25:10. After mixing, the samples were incubated in a thermo mixer for 10 minutes at 70° C. The sample solutions were applied on a 4-12% Bis-Tris gel (NuPAGE™ BisTris, Invitrogen). A sample (10 µl) of marker M12 (Invitrogen) was also applied on the gel. The gel was run at 200V for 50 minutes, using the XCELL Surelock, with 600 ml 20× diluted SDS buffer in the outer buffer chamber and 200 ml 20× diluted SDS buffer, containing 0.5 ml of antioxidant (NuPAGE™ Invitrogen) in the inner buffer chamber. After running, the gel was rinsed twice with demineralised water the gels were fixed with 50% methanol/7% acetic acid solution for one hour and stained with Sypro Ruby (50 ml per gel) overnight. An image was made using the Typhoon 9200 (610 BP 30, Green (532 nm), PMT 600V, 100 micron) after washing the gel with MilliQ water.

Quantitative Analysis of the Protein

Using the Typhoon scanner the ratio between protein bands within a lane was determined using standard methods known in the art. The sample was applied in triplicate and the gray values were determined using the program Image quant. Values are expressed as relative % protein to the total protein, calculated using the gray value of the selected protein band relative to the total gray value all the protein bands.

Glucan Conversion Calculation:

glucan conversion (%)=(glucose (g/l)×100%)/(glucan (fraction on DM)×dm (g/kg)×1.1)

Wherein:
glucose (g/l)=glucose concentration in supernatant after hydrolysis.
glucan (fraction on dm)=glucan content of the substrate before pretreatment.
dm (g/kg)=dry matter of hydrolysis (f.i. 20% dm=200 g/kg).
1.1=weight increase due to water incorporation during hydrolysis.

Example Calculation:
glucose=60 g/l
glucan fraction=0.40 (is 40% on dry matter)
dm=200 g/kg
glucan conversion example=(60*100)/(0.4×200×1.1)=68% conversion Example 1

Evaluation of the Effect of the Absence of Oxygen During Hydrolysis on the Cellulolytic Activity of Cellulase Enzyme Cocktails The effect of oxygen absence during hydrolysis on the cellulolytic activity of three different enzyme cocktails was evaluated according to the procedures described below. The hydrolysis reactions were performed with acid pretreated cornstover (aCS) feedstock at a final concentration of 10 w/w % DM. This feedstock solution was prepared via the dilution of a concentrated feedstock solution with water. Subsequently the pH was adjusted to pH 4.5 with a 4M NaOH solution. The elimination of oxygen from the feedstock was accomplished in two steps. First, the feedstock solution was degassed via sonication under vacuum in a sonication bath (Bransonic 5510E-DTH, setting; Degas) for 15 minutes. In the second step, the oxygen was further removed by continuous sparging of a nitrogen flow through a 500 ml solution of the 10% DM feedstock for a period of 3 hours. Prior to being sparged through the feedstock solution, the nitrogen flow was sparged through water in order to saturate it with water vapour and prevent evaporation of the water from the feedstock solution. In parallel, 500 ml of the same batch 10 w/w % DM aCS was sparged with air as an oxygen-containing control sample in a similar set-up and according to the same protocol.

The hydrolysis of the oxygen-depleted (nitrogen sparged) and the oxygen-saturated (air-sparged) 10 w/w % aCS feedstock solutions were conducted in air-tight, 30-ml centrifuge bottles (Nalgene Oakridge) in a total reaction volume of 10 ml. The bottles, already containing the cellulase solution, used for the oxygen-depleted experiment were sparged with nitrogen prior to-and during filling them with feedstock. Each hydrolysis was performed in duplicate with 7.5 mg/g DM cellulase enzyme cocktail added in a total volume not larger than 375 µl. The three cellulase enzyme cocktails tested included: a TEC-210 mix (mixture of cellulases), a 4E-GH61 mix (consisting of 9 w/w % of total protein BG, 30 w/w % of total protein CBHI, 25 w/w % of total protein CBHII and 36 w/w % of total protein GH61) and a 4E-EG mix (consisting of 9 w/w % of total protein BG, 30 w/w % of total protein CBHI, 25 w/w % of total protein CBHII and 36 w/w % of total protein EG). TEC-210 was fermented according to the inoculation and fermentation procedures described in WO2011/000949. The 4E mix (as described in WO2011/098577) was used.

The centrifuge bottles containing the feedstock and enzyme solution were placed in an oven incubator (Techne HB-1D hybridization oven) and incubated for 72 hours at 65° C. while rotating at set-point 3 (12 rpm per minute). Following hydrolysis, the samples were cooled on ice and immediately 50 µl of each supernatant was diluted in 1450 µl grade I water. The diluted supernatant was subsequently filtered (0.45 µm filter, Pall PN 454) and the filtrates were analysed for sugar content as described below.

The sugar concentrations of the diluted samples were measured using an HPLC equipped with an Aminex HPX-87P column (Biorad #1250098) by elution with water at 85° C. at a flow rate of 0.6 ml per minute and quantified by integration of the glucose signals from refractive index detection (R.I.) calibrated with glucose standard solutions.

The data presented in Table 1/FIG. 1 show that the glucose released from the nitrogen-sparged feedstocks is lower than the glucose released from the feedstocks sparged with air for both the TEC-210 mix and the 4E-GH61 mix incubations. There is no difference in glucose release detectable between the nitrogen and air sparged feedstocks for samples hydrolyzed by the 4E-EG mix.

Based on these results we conclude that the presence of oxygen improves the cellulolytic performance of cellulase mixtures that contain GH61 enzymes.

TABLE 1

The effect of sparging nitrogen or air through a 10% aCS feedstock before hydrolysis, on the total amount of glucose released by three different cellulase mixes.

| Cellulase cocktail | Sparged with air Average glucose (g/l) | stdev | Sparged with $N_2$ Average glucose (g/l) | stdev |
|---|---|---|---|---|
| TEC-210 | 34.5 | 0.8 | 31.9 | 1.1 |
| 4E-GH61 mix | 31.7 | 1.4 | 27.4 | 0.1 |
| 4E-EG mix | 22.7 | 0.1 | 23.3 | 1.7 |

Example 2

The Effect of Oxygen on the Cellulolytic Activity of Cellulase Enzyme Cocktails During Hydrolysis of Lignocellulosic Feedstock The effect of oxygen on the cellulolytic activity of the enzyme cocktail during the hydrolysis of lignocellulosic feedstock is shown in this exaple. The hydrolysis reactions are performed with acid pretreated cornstover (aCS) feedstock at a final concentration of 20 w/w % DM. This feedstock solution is prepared via the dilution of a concentrated feedstock solution with water. Subsequently the pH is adjusted to pH 4.5 with a 10% (w/w) $NH_4OH$ solution.

The hydrolysis is done in a stirred, pH controlled and temperature controlled reactor with a working volume of 1 l. Each hydrolysis is performed in duplicate with 2.5 mg/g DM TEC-210 cellulase enzyme cocktail. TEC-210 was produced according to the inoculation and fermentation procedures described in WO2011/000949.

The following experiments are done:
1. 1 l of 20% aCS, pH 4.5, temperature 62° C., stirrer speed 60 rpm (this corresponds with a DO level of <0.002 mol of oxygen per $m^3$), 2.5 mg/g dm TEC-210 cellulase cocktail, incubation time 120 hours (reference experiment).
2. As experiment 1 but at the start of the hydrolysis, air sparging into the solution started to a dissolved oxygen level of 20% (this corresponds to 0.03 mol of oxygen per m3, measured using a DO (dissolved oxygen) electrode). This dissolved oxygen level is maintained throughout the rest of the hydrolysis process.
3. As experiment 1 but at 72 hours air sparging into the solution started to a dissolved oxygen level of 20% (this corresponds to 0.03 mol of oxygen per m3, measured using a DO (dissolved oxygen) electrode). This dissolved oxygen level is maintained throughout the rest of the hydrolysis process.

After the hydrolysis, the samples are cooled on ice and immediately 50 μl of each supernatant is diluted in 1450 μl grade I water. The diluted supernatant is subsequently filtered (0.45 μm filter, Pall PN 454) and the filtrates are analysed for sugar content as described below.

The sugar concentrations of the diluted samples are measured using an HPLC equipped with an Aminex HPX-87P column (Biorad #1250098) by elution with water at 85° C. at a flow rate of 0.6 ml per minute and quantified by integration of the glucose signals from refractive index detection (R.I.) calibrated with glucose standard solutions.

Figure 2:
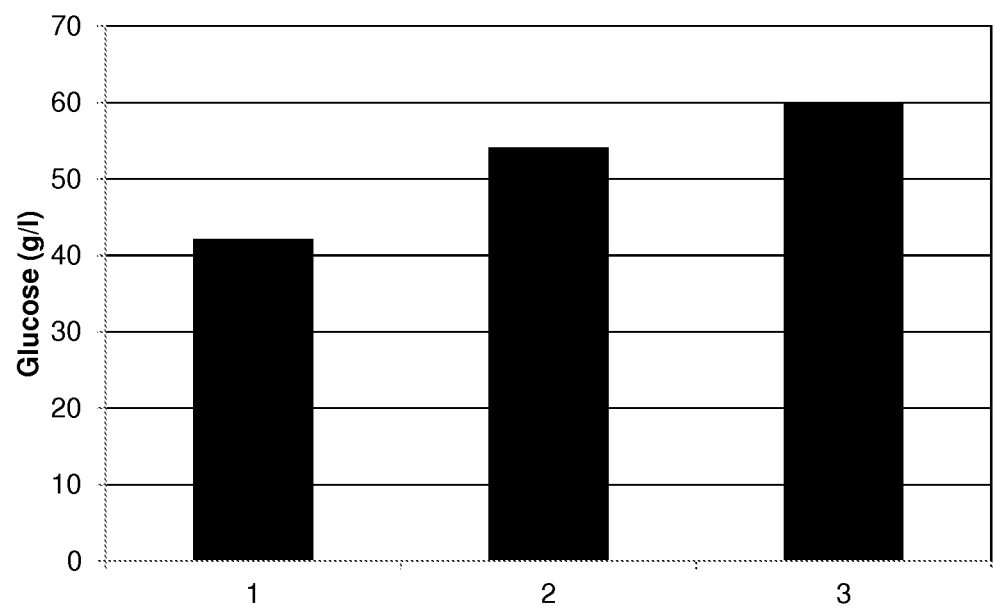
FIG. 2: The glucose produced in Example 2, 1=Experiment 1: no aeration, 2=Experiment 2: continuous aeration, 3=Experiment 3: aeration starting at 72 hours until the end

Results, visible in FIG. 2 clearly show an increased glucose production in case air is added. In addition, air added to the hydrolysis reaction in the second part of the time demonstrates superior glucose production compared to no air addition or an air addition during the whole hydrolysis step.

Example 3

The Effect of Partial Aeration (in Time) on the Enzymatic Hydrolysis of Lignocellulosic Feedstock on Pilot Scale The effect of the dissolved oxygen concentration on the cellulolytic activity of the enzyme cocktail or composition during the hydrolysis of lignocellulosic feedstock on pilot scale is shown in this example. The hydrolysis reactions are performed with acid pretreated cornstover (aCS) feedstock at a final concentration of 20 w/w % DM. The feedstock solution is prepared by the dilution of concentrated feedstock slurry with water. The pH is adjusted to pH 4.5 with a 25% (w/w) $NH_4OH$ solution.

The enzymatic hydrolysis is done in a 270 liter pilot reactor which is pH and temperature controlled with a working volume of 150 liter. The dissolved oxygen during the process is controlled by adjusting impeller speed at a given airflow and overpressure. The enzymatic hydrolysis is performed at a dosage of 2.5 mg (TCA protein)/g dm TEC-210 cellulase enzyme cocktail. TEC-210 was produced according to the inoculation and fermentation procedures described in WO2011/000949.

The following experiments are done:
Experiment 1
Aeration from 0 to 120 hours: 150 l of 20% pCS, pH 4.5, temperature 62° C., 1 bar overpressure, 10 kg/h airflow in the headspace, 3.75 mg TCA/g dm TEC-210 cellulase cocktail, incubation time 120 hours in a 270 liter pilot reactor The dissolved oxygen concentration (DO) of the reaction mixture was measured constantly using a DO electrode. The DO was controlled at a level of 0.15-0.22 mol/$m^3$ by adjusting the impeller speed.
Experment 2
Aeration between 72 and 120 hours: 150 l of 20% pCS, pH 4.5, temperature 62° C., an enzyme dosage 2.50 mg TCA/g dm TEC-210 cellulase cocktail and a total incubation time of 120 hours in a 270 liter pilot reactor. The dissolved oxygen concentration (DO) of the reaction mixture was measured constantly using a DO electrode. For the first 72 hours of the process the following settings were applied: no overpressure, no airflow in the headspace and the DO was controlled at a level of [0.02-0.05] mol/m3 by adjusting the impeller speed. For the last 48 hours of the process the following settings were applied: 1 bar overpressure, 10 kg/h airflow in the headspace and the DO was controlled at a level of 0.15-0.22 mol/$m^3$ by adjusting the impeller speed.

During the enzymatic hydrolysis, samples were taken daily for carbohydrate analysis (glucose, cellobiose) by NMR and viscosity and pH measurement.

Composition analysis of the pretreated Corn Stover was done by chemical hydrolysis of the sample and determination of the mono saccharides by NMR.

Samples taken during enzymatic hydrolysis were analysed for (oligo)sugars, organic acids and inhibitors by flow NMR.

Figure 4:
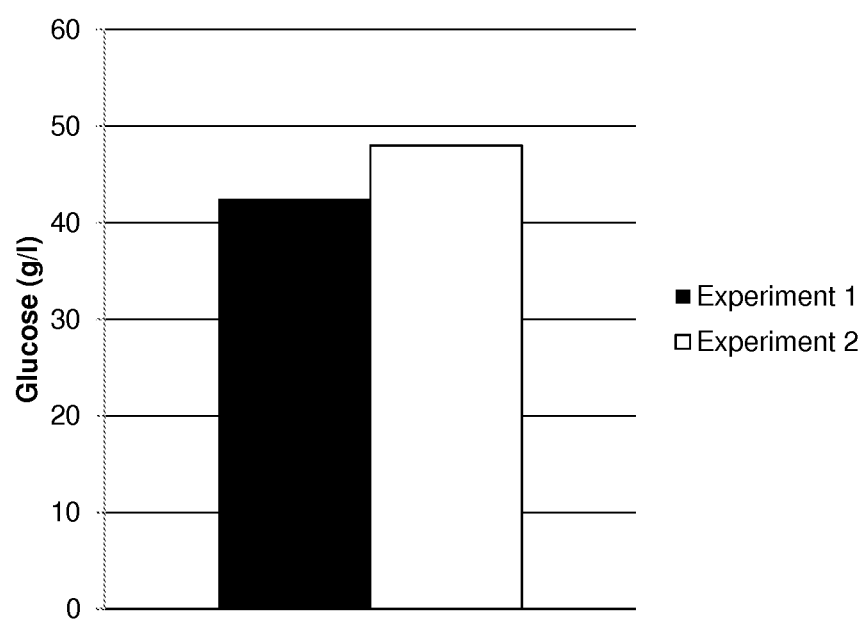
FIG. 4: The effect of time of aeration on glucose produced during enzymatic hydrolysis in experiment 1 (■=aeration between hydrolysis-time is 0 and 100 hours) and 2 (□=aeration between hydrolysis-time is 72 and 100 hours)

The results are presented in FIG. 4 and show that during enzymatic hydrolysis in experiment 2 with the partial aeration (□=aeration between hydrolysis time is 72 and 100 hours) more glucose is produced than during enzymatic hydrolysis in experiment 1 (■=aeration between hydrolysis time is 0 and 100 hours).

Example 4

The Effect of Timing of Dissolved Oxygen Supply on Enzymatic Hydrolysis of Lignocellulosic Feedstock The effect of timing of dissolved oxygen supply on the enzymatic hydrolysis of lignocellulosic feedstock is shown in this example. The hydrolysis reactions are performed with acid pretreated cornstover (aCS) feedstock at a final concentration of 20 w/w % DM. The feedstock solution is prepared by the dilution of concentrated feedstock slurry with water. The pH is adjusted to pH 4.5 with a 25% (w/w) NH$_4$OH solution.

The enzymatic hydrolysis is done in a 2 liter reactor which is pH and temperature controlled with a working volume of 1 liter. The dissolved oxygen during the process is controlled by adjusting impeller speed and continuous refreshment of the headspace with fresh air in case of an increased dissolved oxygen concentration. The enzymatic hydrolysis is performed at a dosage of 1.5 mg (TCA protein)/g dm TEC-210 cellulase enzyme cocktail. TEC-210 was produced according to the inoculation and fermentation procedures described in WO2011/000949.

The following experiments are done:
Experiment 1.
 Aeration from 0 to 7 hours: 1 l of 20% pCS, pH 4.5, temperature 62° C., 1.5 mg TCA/g dm TEC-210 cellulase cocktail, incubation time 120 hours. The dissolved oxygen concentration (DO) of the reaction mixture was measured constantly using a DO electrode. The DO was controlled at a level of >0.05 mol/m$^3$ during the first 7 hours of the hydrolysis process. Between 7 and 120 hours of hydrolysis time the DO was maintained at a level <0.02 mol/m$^3$.

Experiment 2.
 Aeration between 72 and 120 hours: 1 l of 20% pCS, pH 4.5, temperature 62° C., 1.5 mg TCA/g dm TEC-210 cellulase cocktail, incubation time 120 hours. The dissolved oxygen concentration (DO) of the reaction mixture was measured constantly using a DO electrode. The DO was controlled at a level of <0.01 mol/m$^3$ during the first 72 hours of the hydrolysis process. Between 72 and 120 hours of hydrolysis time the DO was maintained at a level >0.05 mol/m$^3$.

During the enzymatic hydrolysis, samples were taken daily for carbohydrate analysis (glucose, cellobiose) by NMR and viscosity and pH measurement.

Composition analysis of the pretreated Corn Stover was done by chemical hydrolysis of the sample and determination of the mono saccharides by NMR.

Figure 5:
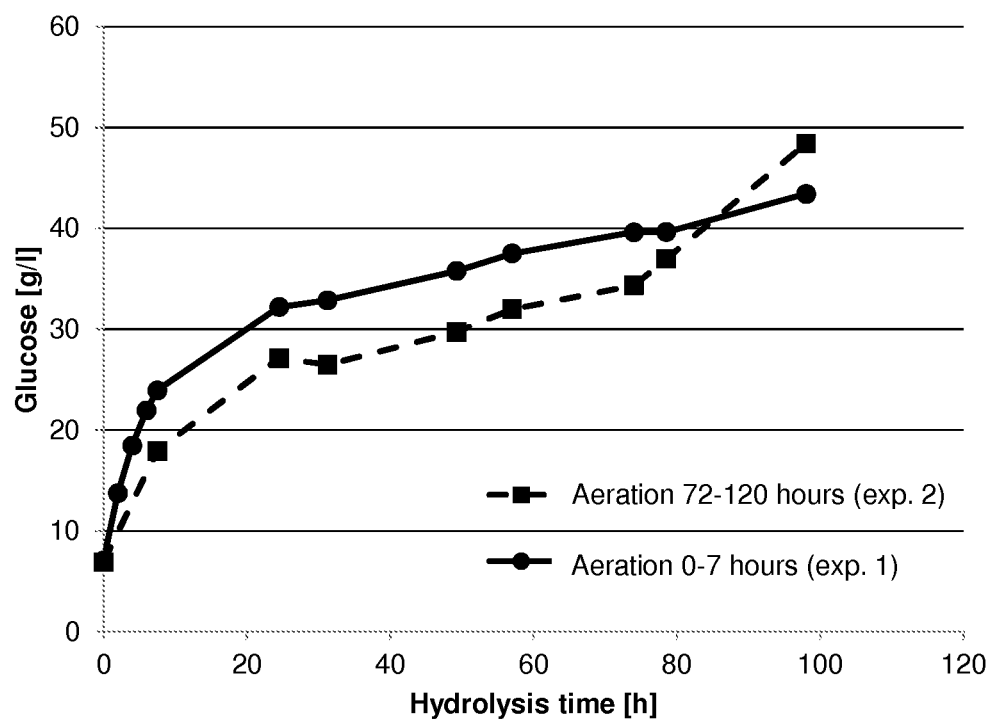
FIG. 5: The effect of time of aeration on glucose produced during enzymatic hydrolysis, —■— aeration between hydrolysis-time is 72 and 100 hours and —●— aeration between hydrolysis-time is 0 and 7 hours

The results are presented in FIG. 5 and clearly demonstrate an increase in the glucose formation rate when the reaction mixture is aerated. Experiment 1, which was aerated between 0 and 7 hours, clearly shows an increased glucose formation rate during the first 7 hours of the process compared with the non-aerated situation during that process phase of Experiment 2. In addition, Experiment 2 demonstrates an increased glucose formation rate between 72 and 120 hours compared with the non-aerated situation during that period in Experiment 1.

Example 5

The Effect of Oxygen on the Cellulolytic Activity of Cellulase Enzyme Compositions During Hydrolysis of Lignocellulosic Feedstock Using a Low Enzyme Dosage The effect of oxygen on the cellulolytic activity of the enzyme composition using a low enzyme dosage during the hydrolysis of lignocellulosic feedstock is shown in this example. The hydrolysis reactions are performed with acid pretreated cornstover (aCS) feedstock at a final concentration of 20 w/w % DM. This feedstock solution is prepared via the dilution of a concentrated feedstock solution with water. Subsequently the pH is adjusted to pH 4.5 with a 10% (w/w) NH$_4$OH solution. The glucan content of the applied corn stover was 37% on dry matter.

The hydrolysis is done in a stirred, pH controlled and temperature controlled reactor with a working volume of 1 l. Each hydrolysis is performed in duplicate with 2.5 mg/g DM of TEC-210 cellulase enzyme composition (or cocktail). TEC-210 was produced according to the inoculation and fermentation procedures described in WO2011/000949.

The following experiments are done:
1. 1 l of 20% aCS, pH 4.5, temperature 62° C., stirrer speed 60 rpm, 3.5 mg TEC-210 cellulase composition per gram feedstock (on dry matter), incubation time 120 hours (reference experiment) in a closed reactor. The dissolved oxygen level of the reaction mixture was measured constantly using a DO electrode. This slow stirring resulted in a dissolved oxygen level 0.005 mol/m$^3$.
2. As experiment 1 but using and enzyme dosage of 2.5 mg TEC-210 per gram feedstock (on dry matter) and a stirrer speed of 250 rpm a head space over the reaction mixture which is constantly refreshed with fresh air. The higher stirring speed in combination with refreshment of the head space with fresh air resulted in a dissolved oxygen level of. 0.030 mol/m$^3$ in the reaction mixture.

During hydrolysis samples were taken for analysis. The samples were cooled on ice and immediately 50 μl of each supernatant is diluted in 1450 μl grade I water. The diluted supernatant is subsequently filtered (0.45 μm filter, Pall PN 454) and the filtrates are analysed for sugar content as described below.

The sugar concentrations of the diluted samples are measured using an HPLC equipped with an Aminex HPX-87P column (Biorad #1250098) by elution with water at 85° C. at a flow rate of 0.6 ml per minute and quantified by integration of the glucose signals from refractive index detection (R.I.) calibrated with glucose standard solutions.

Figure 6:
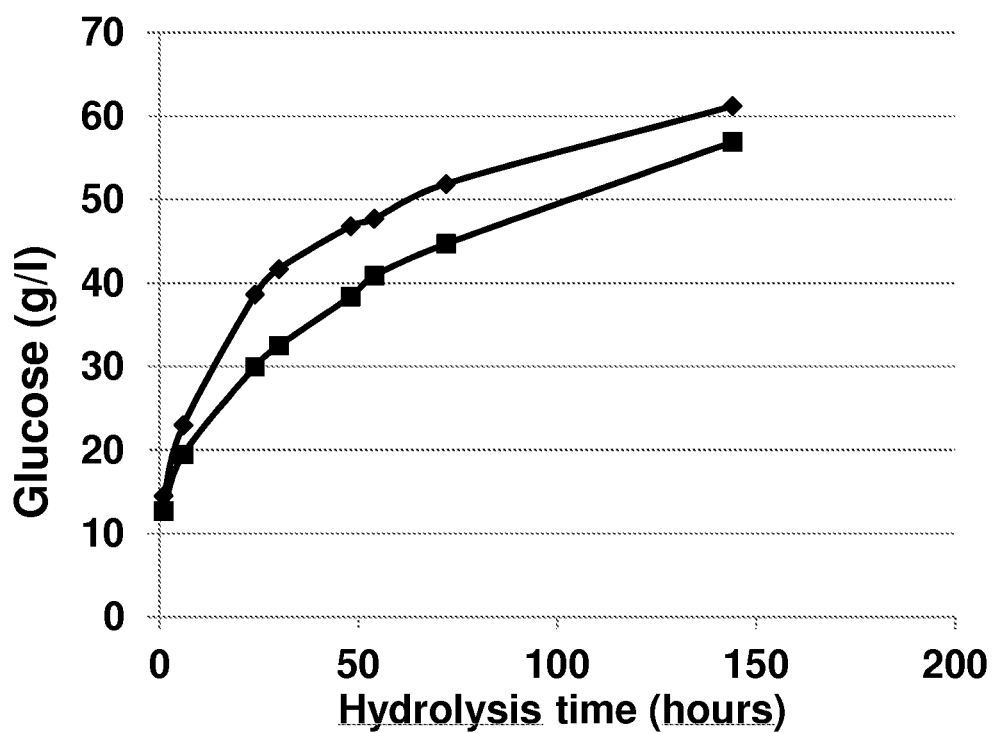
FIG. 6: The effect of the dissolved oxygen concentration (DO) on glucan hydrolysis in pretreated lignocellulosic feedstock as function of hydrolysis time for 2.5 mg/g of enzyme and DO=0.030 mol/m³ (—♦—) and 3.5 mg/g of enzyme and DO=0.005 mol/m³ (—■—).

The results are presented in FIG. 6.
The glucan conversions are listed in Table 2.

TABLE 2 glucan conversion levels.

| Experiment | Enzyme dosage (mg/g dm) | DO level mol/m$^3$ | Glucan conversion (%) |
|---|---|---|---|
| 1 | 2.5 | 0.030 | 75 |
| 2 | 3.5 | 0.005 | 70 |

The invention claimed is:

1. A process for preparation of a sugar product from ligno-cellulosic material, comprising:
    enzymatic hydrolysis, in a reactor, of ligno-cellulosic material using an enzyme composition comprising at least two cellulases and whereby the enzyme composition at least comprises GH61;
    whereby between 0.1 and 7.5 mg enzyme composition/g glucan (on dry matter and enzyme as protein) or between 0.05 and 3.0 mg enzyme composition/g feedstock (on dry matter and enzyme as protein) is used; and
    wherein
        the enzymatic hydrolysis occurs for a first part of time and a subsequent second part of time; and
        (i) during the first part of time oxygen is added to the ligno-cellulosic material to maintain a concentration of dissolved oxygen in the range of 0.02 mol/m$^3$ to 0.12 mol/m$^3$, during the second part of time the concentration of dissolved oxygen is at a concentration at least 50% less than during the first part of time, and the first part of time is 2% to 80% of the total enzymatic hydrolysis time; or
        (ii) during the first part of time dissolved oxygen in the ligno-cellulosic material is at a concentration that is at least 50% less than during the second part of time, during the second part of time oxygen is added to the ligno-cellulosic material to maintain a concentration of dissolved oxygen in the range of 0.02 mol/m$^3$ to 0.12 mol/m$^3$, and the second part of time is 2% to 80% of the total enzymatic hydrolysis time;
    and
    dissolved oxygen is measured under normal atmospheric pressure and at about 62° C.;
    the reactor has a volume of 1 m$^3$ or more; and
    the ligno-cellulosic material has a dry matter content of 10 wt % or more.

2. The process according to claim 1, wherein oxygen is added during the first part of time, and the dissolved oxygen concentration is maintained in the range of 0.02 mol/m$^3$ to 0.045 mol/m$^3$.

3. The process according to claim 1 wherein oxygen is added during the second part of time, and the dissolved oxygen concentration is maintained in the range of 0.02 mol/m$^3$ to 0.045 mol/m$^3$.

4. The process according to claim 1, wherein the enzyme composition used retains activity for 30 hours or more.

5. The process according to claim 1, wherein the hydrolysis is conducted at a temperature of 50° C. or more.

6. The process according to claim 1, wherein the enzyme composition is from a fungus or the enzyme composition comprises a fungal enzyme.

7. The process according to claim 1, wherein the dry matter content is 14 to 33 wt %.

8. A process according to claim 1 in which the enzymatic hydrolysis takes place in a batch, fed batch and/or continuous culture reactor.

9. A process according to claim 1 in which oxygen is introduced as an oxygen-containing gas, in the form of bubbles.

10. The process according to claim 1, wherein the enzyme composition is from a fungus, and the fungus is a microorganism of the genus *Rasamsonia*.

11. The process according to claim 1, wherein the enzyme composition comprises a fungal enzyme, and the fungal enzyme is a *Rasamsonia* enzyme.

12. The process of claim 1, further comprising pre-treatment of the ligno-cellulosic material, prior to the enzymatic hydrolysis.

13. The process of claim 1, further comprising washing of the ligno-cellulosic material, prior to the enzymatic hydrolysis.

14. The process of claim 1, further comprising recovery of a sugar product from the enzymatic hydrolysis.

15. The process of claim 1, further comprising, prior to the enzymatic hydrolysis, pre-treatment of the ligno-cellulosic material and washing of the pre-treated ligno-cellulosic material.

16. The process of claim 1, further comprising pre-treatment of the ligno-cellulosic material prior to the enzymatic hydrolysis and recovery of a sugar product from the enzymatic hydrolysis.

17. The process of claim 1, further comprising pre-treatment of the ligno-cellulosic material and washing of the pre-treated ligno-cellulosic material, prior to the enzymatic hydrolysis, and recovery of a sugar product from the enzymatic hydrolysis.

18. The process of claim 1, wherein oxygen is added during the first part of time, and the first part of time is 2% to 30% of the total enzymatic hydrolysis time.

19. The process of claim 18, wherein first part of time is 5% to 20% of the total enzymatic hydrolysis time.

20. The process of claim 1, wherein oxygen is added during the second part of time, and the second part of time is 12% to 50% of the total enzymatic hydrolysis time.

21. The process of claim 20, wherein the second part of time is 20% to 40% of the total enzymatic hydrolysis time.

22. The process of claim 1, wherein the reactor has a volume of 10 m$^3$ or more.

23. The process of claim 1, wherein the reactor has a volume of 50 m$^3$ or more.

24. The process of claim 1, wherein oxygen is added during the first part of time, and during the second part of time the concentration of dissolved oxygen is at a concentration at least 70% less than during the first part of time.

25. The process of claim 1, wherein oxygen is added during the first part of time, and during the second part of time the concentration of dissolved oxygen is at a concentration at least 90% less than during the first part of time.

26. The process of claim 1, wherein oxygen is added during the second part of time, and during the first part of time the concentration of dissolved oxygen is at a concentration at least 70% less than during the second part of time.

27. The process of claim 1, wherein oxygen is added during the second part of time, and during the first part of time the concentration of dissolved oxygen is at a concentration at least 90% less than during the second part of time.

28. The process of claim 1, further comprising, following said enzymatic hydrolysis, fermentation of the hydrolysed ligno-cellulosic material to produce a fermentation product.

* * * * *